(12) United States Patent
Laus et al.

(10) Patent No.: US 6,194,152 B1
(45) Date of Patent: Feb. 27, 2001

(54) PROSTATE TUMOR POLYNUCLEOTIDE COMPOSITIONS AND METHODS OF DETECTION THEREOF

(75) Inventors: Reiner Laus, San Carlos; Michael H. Shapero, Redwood City; Larisa Tsavaler, Atherton, all of CA (US)

(73) Assignee: Dendreon Corporation, Seattle, WA (US)

( * ) Notice: Subject to any disclaimer, the term of this patent is extended or adjusted under 35 U.S.C. 154(b) by 0 days.

(21) Appl. No.: 09/112,096

(22) Filed: Jul. 9, 1998

Related U.S. Application Data

(60) Provisional application No. 60/056,110, filed on Aug. 20, 1997.

(51) Int. Cl.[7] .............................. C12Q 1/68; C12P 19/34; C12N 15/63; C12N 15/85; C07H 21/04
(52) U.S. Cl. .................... 435/6; 435/91.2; 435/320.1; 435/325; 536/23.1; 536/24.3; 536/24.31; 536/24.33
(58) Field of Search ...................... 435/6, 91.2, 320.1, 435/325; 536/23.1, 24.33, 24.31, 24.3

(56) References Cited

U.S. PATENT DOCUMENTS

| | | |
|---|---|---|
| 5,538,866 | 7/1996 | Israeli et al. . |
| 5,614,372 | 3/1997 | Lilja et al. . |
| 5,672,480 | 9/1997 | Dowell et al. . |
| 5,710,007 | 1/1998 | Luderer et al. . |
| 5,830,649 | * 11/1998 | Bergsma et al. .................... 435/69.1 |

FOREIGN PATENT DOCUMENTS

| | | |
|---|---|---|
| WO 94/09820 | 5/1994 | (WO) . |
| WO 95/30758 | 11/1995 | (WO) . |
| WO 96/30389 | 10/1996 | (WO) . |

OTHER PUBLICATIONS

Levitan, Textbook of Human Genetics, Third Ed., pp. 32–35, 1988.*
Bloch et. al, Geneseq, Accession No. R41668, 1994.*
Kawashima et. al, Geneseq, Accession No. R92050, 1996.*
Hillier et. al, EST, Accession No. AA491471, Aug. 1997.*
International Search Report based on PCT Application No. US98/17058.
Armbruster, D.A., "Prostate–Specific Antigen: Biochemistry, Analytical Methods, and Clinical Application," Clinical Chemistry 39(2): 181–195 (1993).
Blok L.J., et al., "Isolation of cDNAs That Are Differently Expressed Between Androgen–Dependent and Androgen–Independent Prostate Carcinoma Cells Using Differential Display PCR," The Prostate 26:213–224 (1995).
Hillier, L. et al., "Homo sapiens cDNA clone 788034 (AC AA452310)" EMEST8 Database, EMBL Heidelberg, Germany, Jun. 11, 1997, XP002085388.
NCI–CGAP: "Homo sapiens cDNA clone Image: 940638 (accession No. AA493512)," EMEST Database, EMBL Heidelberg, Germany, Jun. 28,1997, XP002098494.
Lundwall, A., and Lilja, H., et al;., "Molecular cloning of human prostate specific antigen," FEBS Lett 214(2):317–322 (1987).

* cited by examiner

*Primary Examiner*—Lisa Arthur
*Assistant Examiner*—Jehanne Souaya
(74) *Attorney, Agent, or Firm*—Linda R. Judge; Peter J. Dehlinger

(57) ABSTRACT

The present invention is directed to novel polynucleotides and the polypeptides encoded by them, each of which are specific to human prostate tumor cells. The present invention further provides chimeric polypeptide molecules comprising the polypeptides of the present invention fused to heterologous polypeptide sequences, and antibodies which bind to the polypeptides of the present invention. Also provided herein are methods for producing the polypeptides of the present invention, as are detection assays that detect the presence of tumor cells in tissue or bodily fluid samples and methods for identifying novel compositions which modulate the activity of prostate tumor antigens and the use of such compositions in diagnosis and treatment of disease.

7 Claims, 5 Drawing Sheets

CTGTATTGGAACGCCTGAAGATTTTCTATTGCTGTCAAGTACCACCTCACTGGG
CCATTCAGCGCCAACTTGCAAGTTTGCTCTTTGAGTTGGGATGTACCAGTTCAGCCC
TTCAGATATTTGAAAAGCTAGAAATGTGGGAAGATGTTGTCATTTGTTRTGAAAGAG
CCGGGCAGCACGGAAAGGCAGAAGAAATCCTTAGACAAGAGCTGGAGAAAAAGAAA
CGCCTAGTTTATACTGCTTGCTTGGAGATGTC

Fig. 1

AGAGGGTTAGAGGACAGGGCCTGGGCACCATCAAATAAGCTTTGGAGTTCCTGTTAG
GGTCGGAGATCTCACTCAGTGTGACATGGGGAGCCTCTCCGGAGGCTTTGGGCAGAA
GAGTGGTATCATCCCACTCAAGTCACGTCGGCTGCCATGTGGTGATGAGGCTATTAG
GTGGCTAGTGTCAAAGAAGGGAGAAGCAGCGTTATATCGGAATGGGCTCCTAC

Fig. 2

AAGGCAGGACTGGATTGTGRTTACRACTGAGTASTAKGCARAGAATTGGARTGTRGG
SAACATAAAKATRATGTSAATMAAATAAGAATGGTCAATTAASACCCTAAAAAAASG
ACRTTCAAAAATGC

Fig. 3

AACACACTTATAAACATTGAGTGCCATTTCCCCCCTACTTTAATAGTCTATTGCTAG
TTCAAGGTTACTTAGCATTTCTTAGGTGACACAACATTCAAAAATGAATGTTTTTCC
ATGCATTTACTATATGCATTCCCTCTCCTGTGAATAATCTATTCATATCCATCTTCT
GGGGACTTGAACCTCTTCTAACTTTGAACAAGCATTTTTTTATGTTACAGATATTAC
TTCTTTGT

Fig. 4

AAATTCATACCTGTGATGGTTCAACAGTTGGAGAAAGGTTCACCTGGAAAGCTGAAA
GTGTTGCTAAATCCACTGAAGGAACAGAAACAATTGAAGGAACAGAAACAATTGAA
GGAGTCTATAACAGTTTTGTTAGCTATTGGTCGTGACTCCTGTACAAGGAAAATAGG
CTTGGAGGAAGATTGGTGTCAAAATTAATGAGAAGAGTGGAAAAATACCTGTA

Fig. 5

CTCGGCAGTGAAAAGCAAGTCATTTCTGGGTCTCTCTGGAAATCAGTCCGCAGGAAS
RCGAGKRGGRRCRCCGAGGGATGATCGTGCCTCCCCCAACCCCAGTGCAATTGTCTG
AACAATTCAGTTCAGATTTCCTACCTCTCTGGGCTCAATCCGAAGCGTTACCTCAGG
ATCTACTGAAGGAACTTTTGCCAGGTGGAAAGCAAACCATGCTCTGTCCAGAGATGA
AGATAAAATTGGCCATGATGA

Fig. 6

TGGCATGACCAGGATTCCTGTGAAAGCAGGAGCAGCAGCAATCCGTCSSGGCGCCTG
CCTTTCCCATCCTTTGGTTCTCCTTTC

Fig. 7

GCTTCTGGTGGTCCTCATTCCATCTTTGCATTCAGATTCAACTGGTTCATGGTTCAT
ACWGGGGGAAACAGGTCCATGGTTGGGATCCATGGGTCCCTCCAGTCTCCTGTTCAA
CGGTCGTACACACCTTGGGAGCACCCACTCGGTTTGTTCATCTTCTGCAAAGATGTC
ATTCTACAGTCATTACCTTCCAGCCTATTTGTTTCTGCAGAATCTACATATACTGTT
GTATCTACCTCAAAATGCAAACACCA

Fig. 8

KFIPVMVQQLEKGSPGKLKVLAKSTEGTETIEG

Fig. 9A

TVLLAIGRDSCTRKIGLE

Fig. 9B

IGVKINEKSGKIPV

Fig. 9C gtcacttaggaaaaggtgtcctttcgggcagccgggctcagcatgaggaa
cagaaggaATGACACTCTGGACAGCACCCGGACCCTGTACTCCAGCGCGT
CTCGGAGCACAGACTTGTCTTACAGTGAAAGCGACTTGGTGAATTTTATT
CAAGCAAATTTTAAGAAACGAGAATGTGTCTTCTTTACCAAAGATTCCAA
GGCCACGGAGAATGTGTGCAAGTGTGGCTATGCCCAGAGCCAGCACATGG
AAGGCACCCAGATCAACCAAAGTGAGAAATGGAACTACAAGAAACACACC
AAGGAATTTCCTACCGACGCCTTTGGGGATATTCAGTTTGAGACACTGGG
GAAGAAAGGGAAGTATATACGTCTGTCCTGCGACACGGACGCGGAAATCC TTTACGAGCTGCTGACCCAGCACTGGCACCTGAAAACACCCAACCTGGTC
ATTTCTGTGACCGGGGGCGCCAAGAACTTCGCCCTGAAGCCGCGCATGCG
CAAGATCTTCAGCCGGCTCATCTACATCGCGCAGTCCAAAGGTGCTTGGA
TTCTCACGGGAGGCACCCATTATGGCCTGACGAAGTACATCGGGGAGGTG
GTGAGAGATAACACCATCAGCAGGAGTTCAGAGGAGAATATTGTGGCCAT
TGGCATAGCAGCTTGGGCATGGTCTCCAACCGGGACACCCTCATCAGGA
ATTGCGATGCTGAGGGCTATTTTTTAGCCCAGTACCTTATGGATGACTTC
ACAAGGGATCCACTGTATATCCTGGACAACAACCACACATTTGCTGCT
CGTGGACAATGGCTGTCATGGACATCCCACTGTCGAAGCAAAGCTCCGGA
ATCAGCTAGAGAAGCATATCTCTGAGCGCACTATTCAAGATTCCAACTAT
GGTGGCAAGATCCCCATTGTGTGTTTTGCCCAAGGAGGTGGAAAAGAGAC
TTTGAAAGCCATCAATACCTCCATCAAAAATAAAATTCCTTGTGTGGTGG
TGGAAGGCTCGGGCCGGATCGCTGATGTGATCGCTAGCCTGGTGGAGGTG
GAGGATGCCCCGACATCTTCTGCCGTCAAGGAGAAGCTGGTGCGCTTTTT
ACCCCGCACGGTGTCCCGGCTGTCTGAGGAGGAGACTGAGAGTTGGATCA
AATGGCTCAAAGAAATTCTCGAATGTTCTCACCTATTAACAGTTATTAAA
ATGGAAGAAGCTGGGGATGAAATTGTGAGCAATGCCATCTCCTACGCTCT
ATACAAAGCCTTCAGCACCAGTGAGCAAGACAAGGATAACTGGAATGGGC
AGCTGAAGCTTCTGCTGGAGTGGAACCAGCTGGACTTAGCCAATGATGAG
ATTTTCACCAATGACCGCCGATGGGAGTCTGCTGACCTTCAAGAAGTCAT
GTTTACGGCTCTCATAAAGGACAGACCCAAGTTTGTCCGCCTCTTTCTGG
AGAATGGCTTGAACCTACGGAAGTTTCTCACCCATGATGTCCTCACTGAA
CTCTTCTCCAACCACTTCAGCACGCTTGTGTAC<u>CGGAATCTGCAGATCGC</u>
<u>CAAGAATTCCTATAATGATGCCCTCCTCACGTTTGTCTGGAAACTGGTTG</u>
<u>CGAACTTCCGAAGAGGCTTCCGGAAGGAAGACAGAAATGGCCGGGACGAG</u>
<u>ATGGACATAGAACTCCACGACGTGTCTCCTATTACTCGGCACCCCCTGCA</u>
<u>AGCTCTCTTCATCTGGGCCATTCTTCAGAATAAGAAGGAACTCTCCAAAG</u>
<u>TCATTTGGGAGCAGACCAGGGGCTGCAC</u>TCTGGCAGCCCTGGGAGCCAGC
AAGCTTCTGAAGACTCTGGCCAAAGTGAAGAACGACATCAATGCTGCTGG
GGAGTCCGAGGAGCTGGCTAATGAGTACGAGACCCGGGCTGTTGAGCTGT
TCACTGAGTGTTACAGCAGCGATGAAGACTTGGCAGAACAGCTGCTGGTC
TATTCCTGTGAAGCTTGGGGTGGAAGCAACTGTCTGGAGCTGGCGGTGGA
GGCCACAGACCAGCATTTCACCGCCCAGCCTGGGGTCCAGAATTTTCTTT
CTAAGCAATGGTATGGAGAGATTTCCCGAGACACCAAGAACTGGAAGATT
ATCCTGTGTCTGTTTATTACCCTTGGTGGGCTGTGGCTTTGTATCATT
TAGGAAGAAACCTGTCGACAAGCACAAGAAGCTGCTTTGGTACTATGTGG
CGTTCTTCACCTCCCCCTTCGTGGTCTTCTCCTGGAATGTGGTCTTCTAC
ATCGCCTTCCTCCTGCTGTTTGCCTACGTGCTGCTCATGGATTTCCATTC
GGTGCCACACCCCCCGAGCTGGTCCTGTACTCGCTGGTCTTTGTCCTCT
TCTGTGATGAAGTGAGACAGTGGTACGTAAATGGGTGAATTATTTTACT
GACCTGTGGAATGTGATGGACACGCTGGGGCTTTTTTACTTCATAGCAGG
AATTGTATTTCGGCTCCACTCTTCTAATAAAAGCTCTTTGTATTCTGGAC
GAGTCATTTTCTGTCTGGACTACATTATTTTCACTCTAAGATTGATCCAC

Fig. 10A

```
ATTTTTACTGTAAGCAGAAACTTAGGACCCAAGATTATAATGCTGCAGAG
GATGCTGATCGATGTGTTCTTCTTCCTGTTCCTCTTTGCGGTGTGGATGG
TGGCCTTTGGCGTGGCCAGGCAAGGGATCCTTAGGCAGAATGAGCAGCGC
TGGAGGTGGATATTCCGTTCGGTCATCTACGAGCCCTACCTGGCCATGTT
CGGCCAGGTGCCCAGTGACGTGGATGGTACCACGTATGACTTTGCCCACT
GCACCTTCACTGGGAATGAGTCCAAGCCACTGTGTGTGGAGCTGGATGAG
CACAACCTGCCCCGGTTCCCCGAGTGGATCACCATCCCCCTGGTGTGCAT
CTACATGTTATCCACCAACATCCTGCTGGTCAACCTGCTGGTCGCCATGT
TTGGCTACACGGTGGGCACCGTCCAGGAGAACAATGACCAGGTCTGGAAG
TTCCAGAGGTACTTCCTGGTGCAGGAGTACTGCAGCCGCCTCAATATCCC
CTTCCCCTTCATCGTCTTCGCTTACTTCTACATGGTGGTGAAGAAGTGCT
TCAAGTGTTGCTGCAAGGAGAAAAACATGGAGTCTTCTGTCTGCTGTTTC
AAAAATGAAGACAATGAGACTCTGGCATGGGAGGGTGTCATGAAGGAAAA
CTACCTTGTCAAGATCAACACAAAAGCCAACGACACCTCAGAGGAAATGA
GGCATCGATTTAGACAACTGGATACAAAGCTTAATGATCTCAAGGGTCTT
CTGAAAGAGATTGCTAATAAAATCAAAtaaaactgtatgaaactctaatg
gagaaaaatctaattatagcaagatcatattaaggaatgctgatgaacaa
ttttgctatcgactactaaatgagagattttcagacccctgggtacatgg
tggatgattttaaatcaccctagtgtgctgagaccttgagaataaagtgt
gtgattggtttcatacttgaagacggatataaaggaagaatatttccttt
atgtgtttctccagaatggtgcctgtttctctctgtgtctcaatgcctgg
gactggaggttgatagtttaagtgtgttcttaccgcctcctttttccttt
aatcttattttgatgaacacatatataggagaacatctatcctatgaat
aagaacctggtcatgctttactcctgtattgttattttgttcatttccaa
ttgattctctacttttcccttttttgtattatgtgactaattagttggca
tattgttaaaagtctctcaaattaggccagattctaaaacatgctgcagc
aagaggacccgctctcttcaggaaaagtgttttcatttctcaggatgct
tcttacctgtcagaggaggtgacaaggcagtctcttgctctcttggactc
accaggctcctattgaaggaaccaccccattcctaaatatgtgaaaagt
cgcccaaaatgcaaccttgaaaggcactactgactttgttcttattggat
actcctcttattttattttttccattaaaaataatagctggctattata
gaaaatttagaccatacagagatgtagaaagaacataaattgtccccatt
accttaaggtaatcactgctaacaatttctggatggtttttcaagtctat
ttttttctatgtatgtctcaattctctttcaaaattttacagaatgtta
tcatactacatatatacttttatgtaagcttttcacttagtatttat
caaatatgttttattatattcatagccttcttaaacattatatcaataa
ttgcataataggcaacctctagcgattaccataattttgctcattgaagg
ctatctccagttgatcattgggatgagcatctttgtgcatgaatcctatt
gctgtatttgggaaaattttccaaggttagattccaataaatatctattt
attattaaatattaaaatatcgatttattattaaaccatttataaggct
ttttcataaatgtatagcaaataggaattattaacttgagcataagatat
gagatacatgaacctgaactattaaaataaaatattatatttaaccctag
tttaagaagaagtcaatatgcttatttaaatattatggatggtgggcaga
tcacttgaggtcaggagttcgagaccagcctggccaacatggcaaaacca
catctctactaaaaataaaaaattagctgggtgtggtggtgcactcctg
taatcccagctactcagaaggctgaggtacaagaattgctggaacctggg
aggcggaggttgcagtgaaccaagattgcaccactgcactccagccgggg
tgacagagtgagactccgactgaaaataaataaataaataaataaa
taaataaataaatattatggatggtgaagggaatggtatagaattggaga
gattatcttactgaacacctgtagtcccagctttctctggaagtggtggt
atttgagcaggatgtgcacaaggcaattgaaatgcccataattagtttct
cagctttgaatacactataaactcagtggctgaaggaggaaattttagaa
```

Fig. 10B

```
ggaagctactaaaagatctaatttgaaaaactacaaaagcattaactaaa
aaagtttatttttccttttgtctgggcagtagtgaaaataactactcacaa
cattcactatgtttgcaaggaattaacacaaataaaagatgcctttttac
ttaaacgccaagacagaaaacttgcccaatactgagaagcaacttgcatt
agagagggaactgttaaatgttttcaacccagttcatctggtggatgttt
ttgcaggttactctgagaattttgcttatgaaaaatcattatttttagtg
tagttcacaataatgtattgaacatacttctaatcaaaggtgctatgtcc
ttgtgtatggtactaaatgtgtcctgtgtactttgcacaactgagaatc
ctgcggcttggtttaatgagtgtgttcatgaaataaataatggaggaatt
gtcaaaaaaaaaaaaaaaaaaaaaaaaaaaaaaaaaaaaaaaaaaaaaa
aaaaaaaaaaaaaaaaa
```

Fig. 10C

```
MRNRRNDTLDSTRTLYSSASRSTDLSYSESDLVNFIQANFKKRECVFFTKDSKATENVCKCGYAQS
QHMEGTQINQSEKWNYKKHTKEFPTDAFGDIQFETLGKKGKYIRLSCDTDAEILYELLTQHWHLKT
PNLVISVTGGAKNFALKPRMRKIFSRLIYIAQSKGAWILTGGTHYGLTKYIGEVVRDNTISRSSEE
NIVAIGIAAWGMVSNRDTLIRNCDAEGYFLAQYLMDDFTRDPLYILDNNHTHLLLVDNGCHGHPTV
EAKLRNQLEKHISERTIQDSNYGGKIPIVCFAQGGGKETLKAINTSIKNKIPCVVVEGSGRIADVI
ASLVEVEDAPTSSAVKEKLVRFLPRTVSRLSEEETESWIKWLKEILECSHLLTVIKMEEAGDEIVS
NAISYALYKAFSTSEQDKDNWNGQLKLLLEWNQLDLANDEIFTNDRRWESADLQEVMFTALIKDRP
KFVRLFLENGLNLRKFLTHDVLTELFSNHFSTLVYRNLQIAKNSYNDALLTFVWKLVANFRRGFRK
EDRNGRDEMDIELHDVSPITRHPLQALFIWAILQNKKELSKVIWEQTRGCTLAALGASKLLKTLAK
VKNDINAAGESEELANEYETRAVELFTECYSSDEDLAEQLLVYSCEAWGGSNCLELAVEATDQHFT
AQPGVQNFLSKQWYGEISRDTKNWKIILCLFIIPLVGCGFVSFRKKPVDKHKKLLWYYVAFFTSPF
VVFSWNVVFYIAFLLLFAYVLLMDFHSVPHPPELVLYSLVFVLFCDEVRQWYVNGVNYFTDLWNVM
DTLGLFYFIAGIVFRLHSSNKSSLYSGRVIFCLDYIIFTLRLIHIFTVSRNLGPKIIMLQRMLIDV
FFFLFLFAVWMVAFGVARQGILRQNEQRWRWIFRSVIYEPYLAMFGQVPSDVDGTTYDFAHCTFTG
NESKPLCVELDEHNLPRFPEWITIPLVCIYMLSTNILLVNLLVAMFGYTVGTVQENNDQVWKFQRY
FLVQEYCSRLNIPFPFIVFAYFYMVVKKCFKCCCKEKNMESSVCCFKNEDNETLAWEGVMKENYLV
KINTKANDTSEEMRHRFRQLDTKLNDLKGLLKEIANKIK
```

Fig. 11

SEQUENCE LISTING

<160> NUMBER OF SEQ ID NOS: 29

<210> SEQ ID NO 1
<211> LENGTH: 257
<212> TYPE: DNA
<213> ORGANISM: Homo sapiens

<400> SEQUENCE: 1

| | | | | | |
|---|---|---|---|---|---|
| ctgtattgga | acgcctgaag | attttctatt | gctgtcaagt | accacctcac | tgggccattc | 60 |
| agcgccaact | tgcaagtttg | ctctttgagt | tgggatgtac | cagttcagcc | cttcagatat | 120 |
| ttgaaaagct | agaaatgtgg | gaagatgttg | tcatttgttr | tgaaagagcc | gggcagcacg | 180 |
| gaaaggcaga | agaaatcctt | agacaagagc | tggagaaaaa | agaaacgcct | agtttatact | 240 |
| gcttgcttgg | agatgtc | | | | | 257 |

<210> SEQ ID NO 2
<211> LENGTH: 224
<212> TYPE: DNA
<213> ORGANISM: Homo sapiens

<400> SEQUENCE: 2

| | | | | | |
|---|---|---|---|---|---|
| agagggttag | aggacagggc | ctgggcacca | tcaaataagc | tttggagttc | ctgttagggt | 60 |
| cggagatctc | actcagtgtg | acatggggag | cctctccgga | ggctttgggc | agaagagtgg | 120 |
| tatcatccca | ctcaagtcac | gtcggctgcc | atgtggtgat | gaggctatta | ggtggctagt | 180 |
| gtcaaagaag | ggagaagcag | cgttatatcg | gaatgggctc | ctac | | 224 |

<210> SEQ ID NO 3
<211> LENGTH: 128
<212> TYPE: DNA
<213> ORGANISM: Homo sapiens

<400> SEQUENCE: 3

| | | | | | |
|---|---|---|---|---|---|
| aaggcaggac | tggattgtgr | ttacractga | gtastakgca | ragaattgga | rtgtrggsaa | 60 |
| cataaakatr | atgtsaatma | aataagaatg | gtcaattaas | accctaaaaa | aasgacrttc | 120 |
| aaaaatgc | | | | | | 128 |

<210> SEQ ID NO 4
<211> LENGTH: 236
<212> TYPE: DNA
<213> ORGANISM: Homo sapiens

<400> SEQUENCE: 4

| | | | | | |
|---|---|---|---|---|---|
| aacacactta | taaacattga | gtgccatttc | ccccctactt | taatagtcta | ttgctagttc | 60 |
| aaggttactt | agcatttctt | aggtgacaca | acattcaaaa | atgaatgttt | ttccatgcat | 120 |
| ttactatatg | cattccctct | cctgtgaata | atctattcat | atccatcttc | tggggacttg | 180 |
| aacctcttct | aactttgaac | aagcattttt | ttatgttaca | gatattactt | ctttgt | 236 |

<210> SEQ ID NO 5
<211> LENGTH: 224
<212> TYPE: DNA
<213> ORGANISM: Homo sapiens

<400> SEQUENCE: 5

| | | | | | |
|---|---|---|---|---|---|
| aaattcatac | ctgtgatggt | tcaacagttg | gagaaaggtt | cacctggaaa | gctgaaagtg | 60 |
| ttggctaaat | ccactgaagg | aacagaaaca | attgaaggaa | cagaaacaat | tgaaggagtc | 120 |

```
tataacagtt tgttagcta ttggtcgtga ctcctgtaca aggaaaatag gcttggagga    180
agattggtgt caaaattaat gagaagagtg gaaaaatacc tgta                   224
```

<210> SEQ ID NO 6
<211> LENGTH: 249
<212> TYPE: DNA
<213> ORGANISM: Homo sapiens

<400> SEQUENCE: 6

```
ctcggcagtg aaaagcaagt catttctggg tctctctgga aatcagtccg caggaasrcg    60
agkrggrrcr ccgagggatg atcgtgcctc ccccaacccc agtgcaattg tctgaacaat   120
tcagttcaga tttcctacct ctctgggctc aatccgaagc gttacctcag gatctactga   180
aggaactttt gccaggtgga aagcaaacca tgctctgtcc agagatgaag ataaaattgg   240
ccatgatga                                                          249
```

<210> SEQ ID NO 7
<211> LENGTH: 84
<212> TYPE: DNA
<213> ORGANISM: Homo sapiens

<400> SEQUENCE: 7

```
tggcatgacc aggattcctg tgaaagcagg agcagcagca atccgtcssg gcgcctgcct    60
ttcccatcct ttggttctcc tttc                                          84
```

<210> SEQ ID NO 8
<211> LENGTH: 254
<212> TYPE: DNA
<213> ORGANISM: Homo sapiens

<400> SEQUENCE: 8

```
gcttctggtg gtcctcattc catctttgca ttcagattca actggttcat ggttcatacw    60
gggggaaaca ggtccatggt tgggatccat gggtccctcc agtctcctgt tcaacggtcg   120
tacacacctt gggagcaccc actcggtttg ttcatcttct gcaaagatgt cattctacag   180
tcattacctt ccagcctatt tgtttctgca gaatctacat atactgttgt atctacctca   240
aaatgcaaac acca                                                    254
```

<210> SEQ ID NO 9
<211> LENGTH: 33
<212> TYPE: PRT
<213> ORGANISM: Homo sapiens

<400> SEQUENCE: 9

```
Lys Phe Ile Pro Val Met Val Gln Gln Leu Glu Lys Gly Ser Pro Gly
 1               5                  10                  15

Lys Leu Lys Val Leu Ala Lys Ser Thr Glu Gly Thr Glu Thr Ile Glu
            20                  25                  30

Gly
```

<210> SEQ ID NO 10
<211> LENGTH: 18
<212> TYPE: PRT
<213> ORGANISM: Homo sapiens

<400> SEQUENCE: 10

```
Thr Val Leu Leu Ala Ile Gly Arg Asp Ser Cys Thr Arg Lys Ile Gly
 1               5                  10                  15
```

-continued

Leu Glu

<210> SEQ ID NO 11
<211> LENGTH: 14
<212> TYPE: PRT
<213> ORGANISM: Homo sapiens

<400> SEQUENCE: 11

Ile Gly Val Lys Ile Asn Glu Lys Ser Gly Lys Ile Pro Val
 1               5                  10

<210> SEQ ID NO 12
<211> LENGTH: 17
<212> TYPE: DNA
<213> ORGANISM: Artificial Sequence
<220> FEATURE:
<221> NAME/KEY: primer_bind
<222> LOCATION: (1)...(17)
<223> OTHER INFORMATION: oligonucleotide primer

<400> SEQUENCE: 12
acgactcact ataggqc                                                      17

<210> SEQ ID NO 13
<211> LENGTH: 16
<212> TYPE: DNA
<213> ORGANISM: Artificial Sequence
<220> FEATURE:
<221> NAME/KEY: primer_bind
<222> LOCATION: (1)...(16)
<223> OTHER INFORMATION: oligonucleotide primer

<400> SEQUENCE: 13
acaatttcac acagca                                                       16

<210> SEQ ID NO 14
<211> LENGTH: 5668
<212> TYPE: DNA
<213> ORGANISM: Homo sapiens

<400> SEQUENCE: 14
gtcacttagg aaaagtgtc ctttcgggca gccgggctca gcatgaggaa cagaaggaat        60
gacactctgg acagcacccg gaccctgtac tccagcgcgt ctcggagcac agacttgtct      120
tacagtgaaa gcgacttggt gaattttatt caagcaaatt ttaagaaacg agaatgtgtc      180
ttctttacca aagattccaa ggccacggag aatgtgtgca agtgtggcta tgcccagagc      240
cagcacatgg aaggcaccca gatcaaccaa agtgagaaat ggaactacaa gaaacacacc      300
aaggaatttc ctaccgacgc ctttggggat attcagtttg agacactggg gaagaaaggg      360
aagtatatac gtctgtcctg cgacacggac gcggaaatcc tttacgagct gctgacccag      420
cactggcacc tgaaaacacc caacctggtc atttctgtga ccgggggcgc caagaacttc      480
gccctgaagc cgcgcatgcg caagatcttc agccggctca tctacatcgc gcagtccaaa      540
ggtgcttgga ttctcacggg aggcacccat tatgcctga cgaagtacat cggggaggtg      600
gtgagagata acaccatcag caggagttca gaggagaata ttgtggccat ggcatagca      660 gcttggggca tggtctccaa ccgggacacc ctcatcagga attgcgatgc tgagggctat      720
tttttagccc agtaccttat ggatgacttc acaagggatc cactgtatat cctgacaac      780 aaccacacac atttgctgct cgtggacaat ggctgtcatg acatccac tgtcgaagca      840 aagctccgga atcagctaga gaagcatatc tctgagcgca ctattcaaga ttccaactat      900

-continued

```
ggtggcaaga tccccattgt gtgttttgcc caaggaggtg gaaaagagac tttgaaagcc      960
atcaatacct ccatcaaaaa taaaattcct tgtgtggtgg tggaaggctc gggccggatc     1020
gctgatgtga tcgctagcct ggtggaggtg gaggatgccc cgacatcttc tgccgtcaag     1080
gagaagctgg tgcgcttttt accccgcacg gtgtcccggc tgtctgagga ggagactgag     1140
agttggatca aatggctcaa agaaattctc gaatgttctc acctattaac agttattaaa     1200
atggaagaag ctgggatga aattgtgagc aatgccatct cctacgctct atacaaagcc      1260
ttcagcacca gtgagcaaga caaggataac tggaatggga gctgaagct tctgctggag      1320 tggaaccagc tggacttagc caatgatgag attttcacca atgaccgccg atgggagtct     1380
gctgaccttc aagaagtcat gtttacggct ctcataaagg acagacccaa gtttgtccgc     1440
ctctttctgg agaatggctt gaacctacgg aagtttctca cccatgatgt cctcactgaa     1500
ctcttctcca accacttcag cacgcttgtg taccggaatc tgcagatcgc caagaattcc     1560
tataatgatg ccctcctcac gtttgtctgg aaactggttg cgaacttccg aagaggcttc     1620
cggaaggaag acagaaatgg ccgggacgag atggacatag aactccacga cgtgtctcct     1680
attactcggc accccctgca agctctcttc atctgggcca ttcttcagaa taagaaggaa     1740
ctctccaaag tcatttggga gcagaccagg ggctgcactc tggcagccct gggagccagc     1800
aagcttctga agactctggc caaagtgaag aacgacatca atgctgctgg ggagtccgag     1860
gagctggcta atgagtacga gacccgggct gttgagctgt tcactgagtg ttacagcagc     1920
gatgaagact tggcagaaca gctgctggtc tattcctgtg aagcttgggg tggaagcaac     1980
tgtctggagc tggcggtgga ggccacagac cagcatttca ccgcccagcc tggggtccag     2040
aattttcttt ctaagcaatg gtatggagag atttcccgag acaccaagaa ctggaagatt     2100
atcctgtgtc tgtttattat acccttggtg ggctgtggct ttgtatcatt taggaagaaa     2160
cctgtcgaca agcacaagaa gctgctttgg tactatgtgg cgttcttcac ctcccccttc     2220
gtggtcttct cctggaatgt ggtcttctac atcgccttcc tcctgctgtt tgcctacgtg     2280
ctgctcatgg atttccattc ggtgccacac ccccccgagc tggtcctgta ctcgctggtc     2340
tttgtcctct tctgtgatga agtgagacag tggtacgtaa atggggtgaa ttattttact     2400
gacctgtgga atgtgatgga cacgctgggg cttttttact tcatagcagg aattgtattt     2460
cggctccact cttctaataa aagctctttg tattctggac gagtcatttt ctgtctggac     2520
tacattattt tcactctaag attgatccac atttttactg taagcagaaa cttaggaccc     2580
aagattataa tgctgcagag gatgctgatc gatgtgttct tcttcctgtt cctctttgcg     2640
gtgtggatgg tggcctttgg cgtggccagg caagggatcc ttaggcagaa tgagcagcgc     2700
tggaggtgga tattccgttc ggtcatctac gagccctacc tggccatgtt cggccaggtg     2760
cccagtgacg tggatggtac cacgtatgac tttgcccact gcaccttcac tgggaatgag     2820
tccaagccac tgtgtgtgga gctggatgag cacaacctgc cccggttccc cgagtggatc     2880
accatccccc tggtgtgcat ctacatgtta tccaccaaca tcctgctggt caacctgctg     2940
gtcgccatgt ttggctacac ggtgggcacc gtccaggaga caatgaccca ggtctggaag     3000
ttccagaggt acttcctggt gcaggagtac tgcagccgcc tcaatatccc cttccccttc     3060
atcgtcttcg cttacttcta catggtggtg aagaagtgct tcaagtgttg ctgcaaggag     3120
aaaaacatgg agtcttctgt ctgctgtttc aaaaatgaag acaatgagac tctggcatgg     3180
gagggtgtca tgaaggaaaa ctaccttgtc aagatcaaca caaaagccaa cgacacctca     3240
```

```
gaggaaatga ggcatcgatt tagacaactg gatacaaagc ttaatgatct caagggtctt   3300
ctgaaagaga ttgctaataa aatcaaataa aactgtatga aactctaatg gagaaaaatc   3360
taattatagc aagatcatat taaggaatgc tgatgaacaa ttttgctatc gactactaaa   3420
tgagagattt tcagacccct gggtacatgg tggatgattt taaatcaccc tagtgtgctg   3480
agaccttgag aataaagtgt gtgattggtt tcatacttga agacggatat aaaggaagaa   3540
tatttccttt atgtgtttct ccagaatggt gcctgtttct ctctgtgtct caatgcctgg   3600
gactggaggt tgatagttta agtgtgttct taccgcctcc ttttccttt aatcttattt    3660 ttgatgaaca catatatagg agaacatcta tcctatgaat aagaacctgg tcatgcttta   3720
ctcctgtatt gttattttgt tcatttccaa ttgattctct acttttccct tttttgtatt   3780
atgtgactaa ttagttggca tattgttaaa agtctctcaa attaggccag attctaaaac   3840
atgctgcagc aagaggaccc cgctctcttc aggaaaagtg ttttcatttc tcaggatgct   3900
tcttacctgt cagaggaggt gacaaggcag tctcttgctc tcttggactc accaggctcc   3960
tattgaagga accaccccca ttcctaaata tgtgaaaagt cgcccaaaat gcaaccttga   4020
aaggcactac tgactttgtt cttattggat actcctctta tttattattt ttccattaaa   4080
aataatagct ggctattata gaaaatttag accatacaga gatgtagaaa gaacataaat   4140
tgtccccatt accttaaggt aatcactgct aacaatttct ggatggtttt tcaagtctat   4200
tttttttcta tgtatgtctc aattctcttt caaaattta cagaatgtta tcatactaca    4260
tatatacttt ttatgtaagc tttttcactt agtattttat caaatatgtt tttattatat   4320
tcatagcctt cttaaacatt atatcaataa ttgcataata ggcaacctct agcgattacc   4380
ataattttgc tcattgaagg ctatctccag ttgatcattg ggatgagcat ctttgtgcat   4440
gaatcctatt gctgtatttg ggaaaatttt ccaaggttag attccaataa atatctattt   4500
attattaaat attaaaatat cgattttatta ttaaaaccat ttataaggct ttttcataaa   4560
tgtatagcaa ataggaatta ttaacttgag cataagatat gagatacatg aacctgaact   4620
attaaaataa aatattatat ttaaccctag tttaagaaga agtcaatatg cttatttaaa   4680
tattatggat ggtgggcaga tcacttgagg tcaggagttc gagaccagcc tggccaacat   4740
ggcaaaacca catctctact aaaaataaaa aaattagctg ggtgtggtgg tgcactcctg   4800
taatcccagc tactcagaag gctgaggtac aagaattgct ggaacctggg aggcggaggt   4860
tgcagtgaac caagattgca ccactgcact ccagccgggg tgacagagtg agactccgac   4920
tgaaaataaa taaataaata aataaataaa taaataaata aatattatgg atggtgaagg   4980
gaatggtata gaattggaga gattatctta ctgaacacct gtagtcccag ctttctctgg   5040
aagtggtggt atttgagcag gatgtgcaca aggcaattga aatgcccata attagtttct   5100
cagctttgaa tacactataa actcagtggc tgaaggagga aatttttagaa ggaagctact  5160 aaaagatcta atttgaaaaa ctacaaaagc attaactaaa aaagtttatt ttccttttgt   5220
ctgggcagta gtgaaaataa ctactcacaa cattccactat gtttgcaagg aattaacaca   5280
aataaaagat gccttttttac ttaaacgcca agacagaaaa cttgcccaat actgagaagc  5340
aacttgcatt agagagggaa ctgttaaatg ttttcaaccc agttcatctg gtggatgttt   5400
ttgcaggtta ctctgagaat tttgcttatg aaaaatcatt atttttagtg tagttcacaa   5460
taatgtattg aacatacttc taatcaaagg tgctatgtcc ttgtgtatgg tactaaatgt   5520
gtcctgtgta cttttgcaca actgagaatc ctgcggcttg gtttaatgag tgtgttcatg   5580
aaataaataa tggaggaatt gtcaaaaaaa aaaaaaaaaa aaaaaaaaaa aaaaaaaaa    5640
```
aaaaaaaaaa aaaaaaaaaa aaaaaaaa                                                      5668

<210> SEQ ID NO 15
<211> LENGTH: 1095
<212> TYPE: PRT
<213> ORGANISM: Homo sapiens

<400> SEQUENCE: 15

```
Met Arg Asn Arg Arg Asn Asp Thr Leu Asp Ser Thr Arg Thr Leu Tyr
 1               5                  10                  15

Ser Ser Ala Ser Arg Ser Thr Asp Leu Ser Tyr Ser Glu Ser Asp Leu
            20                  25                  30

Val Asn Phe Ile Gln Ala Asn Phe Lys Lys Arg Glu Cys Val Phe Phe
        35                  40                  45

Thr Lys Asp Ser Lys Ala Thr Glu Asn Val Cys Lys Cys Gly Tyr Ala
 50                  55                  60

Gln Ser Gln His Met Glu Gly Thr Gln Ile Asn Gln Ser Glu Lys Trp
 65                  70                  75                  80

Asn Tyr Lys Lys His Thr Lys Glu Phe Pro Thr Asp Ala Phe Gly Asp
                85                  90                  95

Ile Gln Phe Glu Thr Leu Gly Lys Lys Gly Lys Tyr Ile Arg Leu Ser
            100                 105                 110

Cys Asp Thr Asp Ala Glu Ile Leu Tyr Glu Leu Leu Thr Gln His Trp
        115                 120                 125

His Leu Lys Thr Pro Asn Leu Val Ile Ser Val Thr Gly Gly Ala Lys
130                 135                 140

Asn Phe Ala Leu Lys Pro Arg Met Arg Lys Ile Phe Ser Arg Leu Ile
145                 150                 155                 160

Tyr Ile Ala Gln Ser Lys Gly Ala Trp Ile Leu Thr Gly Gly Thr His
                165                 170                 175

Tyr Gly Leu Thr Lys Tyr Ile Gly Glu Val Val Arg Asp Asn Thr Ile
            180                 185                 190

Ser Arg Ser Ser Glu Glu Asn Ile Val Ala Ile Gly Ile Ala Ala Trp
        195                 200                 205

Gly Met Val Ser Asn Arg Asp Thr Leu Ile Arg Asn Cys Asp Ala Glu
210                 215                 220

Gly Tyr Phe Leu Ala Gln Tyr Leu Met Asp Asp Phe Thr Arg Asp Pro
225                 230                 235                 240

Leu Tyr Ile Leu Asp Asn Asn His Thr His Leu Leu Leu Val Asp Asn
                245                 250                 255

Gly Cys His Gly His Pro Thr Val Glu Ala Lys Leu Arg Asn Gln Leu
            260                 265                 270

Glu Lys His Ile Ser Glu Arg Thr Ile Gln Asp Ser Asn Tyr Gly Gly
        275                 280                 285

Lys Ile Pro Ile Val Cys Phe Ala Gln Gly Gly Gly Lys Glu Thr Leu
290                 295                 300

Lys Ala Ile Asn Thr Ser Ile Lys Asn Lys Ile Pro Cys Val Val Val
305                 310                 315                 320

Glu Gly Ser Gly Arg Ile Ala Asp Val Ile Ala Ser Leu Val Glu Val
                325                 330                 335

Glu Asp Ala Pro Thr Ser Ser Ala Val Lys Glu Lys Leu Val Arg Phe
            340                 345                 350

Leu Pro Arg Thr Val Ser Arg Leu Ser Glu Glu Glu Thr Glu Ser Trp
        355                 360                 365
```

-continued

```
Ile Lys Trp Leu Lys Glu Ile Leu Glu Cys Ser His Leu Leu Thr Val
    370             375                 380
Ile Lys Met Glu Glu Ala Gly Asp Glu Ile Val Ser Asn Ala Ile Ser
385                 390                 395                 400
Tyr Ala Leu Tyr Lys Ala Phe Ser Thr Ser Glu Gln Asp Lys Asp Asn
                405                 410                 415
Trp Asn Gly Gln Leu Lys Leu Leu Glu Trp Asn Gln Leu Asp Leu
                420                 425                 430
Ala Asn Asp Glu Ile Phe Thr Asn Asp Arg Arg Trp Glu Ser Ala Asp
        435                 440                 445
Leu Gln Glu Val Met Phe Thr Ala Leu Ile Lys Asp Arg Pro Lys Phe
    450                 455                 460
Val Arg Leu Phe Leu Glu Asn Gly Leu Asn Leu Arg Lys Phe Leu Thr
465                 470                 475                 480
His Asp Val Leu Thr Glu Leu Phe Ser Asn His Phe Ser Thr Leu Val
                485                 490                 495
Tyr Arg Asn Leu Gln Ile Ala Lys Asn Ser Tyr Asn Asp Ala Leu Leu
                500                 505                 510
Thr Phe Val Trp Lys Leu Val Ala Asn Phe Arg Arg Gly Phe Arg Lys
        515                 520                 525
Glu Asp Arg Asn Gly Arg Asp Glu Met Asp Ile Glu Leu His Asp Val
    530                 535                 540
Ser Pro Ile Thr Arg His Pro Leu Gln Ala Leu Phe Ile Trp Ala Ile
545                 550                 555                 560
Leu Gln Asn Lys Lys Glu Leu Ser Lys Val Ile Trp Glu Gln Thr Arg
                565                 570                 575
Gly Cys Thr Leu Ala Ala Leu Gly Ala Ser Lys Leu Leu Lys Thr Leu
                580                 585                 590
Ala Lys Val Lys Asn Asp Ile Asn Ala Ala Gly Glu Ser Glu Glu Leu
        595                 600                 605
Ala Asn Glu Tyr Glu Thr Arg Ala Val Glu Leu Phe Thr Glu Cys Tyr
    610                 615                 620
Ser Ser Asp Glu Asp Leu Ala Glu Gln Leu Leu Val Tyr Ser Cys Glu
625                 630                 635                 640
Ala Trp Gly Gly Ser Asn Cys Leu Glu Leu Ala Val Glu Ala Thr Asp
                645                 650                 655
Gln His Phe Thr Ala Gln Pro Gly Val Gln Asn Phe Leu Ser Lys Gln
                660                 665                 670
Trp Tyr Gly Glu Ile Ser Arg Asp Thr Lys Asn Trp Lys Ile Ile Leu
        675                 680                 685
Cys Leu Phe Ile Ile Pro Leu Val Gly Cys Gly Phe Val Ser Phe Arg
    690                 695                 700
Lys Lys Pro Val Asp Lys His Lys Lys Leu Leu Trp Tyr Tyr Val Ala
705                 710                 715                 720
Phe Phe Thr Ser Pro Phe Val Val Phe Ser Trp Asn Val Val Phe Tyr
                725                 730                 735
Ile Ala Phe Leu Leu Leu Phe Ala Tyr Val Leu Leu Met Asp Phe His
                740                 745                 750
Ser Val Pro His Pro Pro Glu Leu Val Leu Tyr Ser Leu Val Phe Val
        755                 760                 765
Leu Phe Cys Asp Glu Val Arg Gln Trp Tyr Val Asn Gly Val Asn Tyr
    770                 775                 780
```

Phe Thr Asp Leu Trp Asn Val Met Asp Thr Leu Gly Leu Phe Tyr Phe
785                 790                 795                 800

Ile Ala Gly Ile Val Phe Arg Leu His Ser Ser Asn Lys Ser Ser Leu
            805                 810                 815

Tyr Ser Gly Arg Val Ile Phe Cys Leu Asp Tyr Ile Ile Phe Thr Leu
            820                 825                 830

Arg Leu Ile His Ile Phe Thr Val Ser Arg Asn Leu Gly Pro Lys Ile
            835                 840                 845

Ile Met Leu Gln Arg Met Leu Ile Asp Val Phe Phe Leu Phe Leu
850                 855                 860

Phe Ala Val Trp Met Val Ala Phe Gly Val Ala Arg Gln Gly Ile Leu
865                 870                 875                 880

Arg Gln Asn Glu Gln Arg Trp Arg Trp Ile Phe Arg Ser Val Ile Tyr
                885                 890                 895

Glu Pro Tyr Leu Ala Met Phe Gly Gln Val Pro Ser Asp Val Asp Gly
                900                 905                 910

Thr Thr Tyr Asp Phe Ala His Cys Thr Phe Thr Gly Asn Glu Ser Lys
            915                 920                 925

Pro Leu Cys Val Glu Leu Asp Glu His Asn Leu Pro Arg Phe Pro Glu
930                 935                 940

Trp Ile Thr Ile Pro Leu Val Cys Ile Tyr Met Leu Ser Thr Asn Ile
945                 950                 955                 960

Leu Leu Val Asn Leu Leu Val Ala Met Phe Gly Tyr Thr Val Gly Thr
                965                 970                 975

Val Gln Glu Asn Asn Asp Gln Val Trp Lys Phe Gln Arg Tyr Phe Leu
                980                 985                 990

Val Gln Glu Tyr Cys Ser Arg Leu Asn Ile Pro Phe Pro Phe Ile Val
            995                 1000                1005

Phe Ala Tyr Phe Tyr Met Val Val Lys Lys Cys Phe Lys Cys Cys
    1010                1015                1020

Lys Glu Lys Asn Met Glu Ser Ser Val Cys Cys Phe Lys Asn Glu Asp
1025                1030                1035                104

Asn Glu Thr Leu Ala Trp Glu Gly Val Met Lys Glu Asn Tyr Leu Val
            1045                1050                1055

Lys Ile Asn Thr Lys Ala Asn Asp Thr Ser Glu Glu Met Arg His Arg
            1060                1065                1070

Phe Arg Gln Leu Asp Thr Lys Leu Asn Asp Leu Lys Gly Leu Leu Lys
        1075                1080                1085

Glu Ile Ala Asn Lys Ile Lys
    1090                1095

<210> SEQ ID NO 16
<211> LENGTH: 22
<212> TYPE: DNA
<213> ORGANISM: Artificial Sequence
<220> FEATURE:
<221> NAME/KEY: primer_bind
<222> LOCATION: (1)...(22)
<223> OTHER INFORMATION: NP1 primer

<400> SEQUENCE: 16
tcgagcggcc gcccgggcag gt                                         22

<210> SEQ ID NO 17
<211> LENGTH: 22
<212> TYPE: DNA
<213> ORGANISM: Artificial Sequence

```
<220> FEATURE:
<221> NAME/KEY: primer_bind
<222> LOCATION: (1)...(22)
<223> OTHER INFORMATION: NP2 primer

<400> SEQUENCE: 17
agggcgtggt gcggagggcg gt                                              22

<210> SEQ ID NO 18
<211> LENGTH: 16
<212> TYPE: DNA
<213> ORGANISM: Artificial Sequence
<220> FEATURE:
<221> NAME/KEY: primer_bind
<222> LOCATION: (1)...(16)
<223> OTHER INFORMATION: M13 reverse primer

<400> SEQUENCE: 18
caggaaacag ctatga                                                     16

<210> SEQ ID NO 19
<211> LENGTH: 18
<212> TYPE: DNA
<213> ORGANISM: Artificial Sequence
<220> FEATURE:
<221> NAME/KEY: primer_bind
<222> LOCATION: (1)...(18)
<223> OTHER INFORMATION: M13 forward primer

<400> SEQUENCE: 19
gtaaaacgac ggccagtg                                                   18

<210> SEQ ID NO 20
<211> LENGTH: 27
<212> TYPE: DNA
<213> ORGANISM: Artificial Sequence
<220> FEATURE:
<221> NAME/KEY: primer_bind
<222> LOCATION: (1)...(27)
<223> OTHER INFORMATION: AP1 primer

<400> SEQUENCE: 20
ccatcctaat acgactcact atagggc                                         27

<210> SEQ ID NO 21
<211> LENGTH: 26
<212> TYPE: DNA
<213> ORGANISM: Artificial Sequence
<220> FEATURE:
<221> NAME/KEY: primer_bind
<222> LOCATION: (1)...(26)
<223> OTHER INFORMATION: A79331 primer

<400> SEQUENCE: 21
gccgagtaat aggagacacg tcgtgg                                          26

<210> SEQ ID NO 22
<211> LENGTH: 23
<212> TYPE: DNA
<213> ORGANISM: Artificial Sequence
<220> FEATURE:
<221> NAME/KEY: primer_bind
<222> LOCATION: (1)...(23)
<223> OTHER INFORMATION: A79326 primer

<400> SEQUENCE: 22
tggaaactgg ttgcgaactt ccg                                             23
```

-continued

```
<210> SEQ ID NO 23
<211> LENGTH: 23
<212> TYPE: DNA
<213> ORGANISM: Artificial Sequence
<220> FEATURE:
<221> NAME/KEY: primer_bind
<222> LOCATION: (1)...(23)
<223> OTHER INFORMATION: AP2 primer

<400> SEQUENCE: 23
actcactata gggctcgagc ggc                                              23

<210> SEQ ID NO 24
<211> LENGTH: 25
<212> TYPE: DNA
<213> ORGANISM: Artificial Sequence
<220> FEATURE:
<221> NAME/KEY: primer_bind
<222> LOCATION: (1)...(25)
<223> OTHER INFORMATION: A79328 primer

<400> SEQUENCE: 24
caaagtcatt tggcagcaga ccagg                                            25

<210> SEQ ID NO 25
<211> LENGTH: 21
<212> TYPE: DNA
<213> ORGANISM: Artificial Sequence
<220> FEATURE:
<221> NAME/KEY: primer_bind
<222> LOCATION: (1)...(21)
<223> OTHER INFORMATION: A80552 primer

<400> SEQUENCE: 25
gattttcacc aatgaccgcc g                                                21

<210> SEQ ID NO 26
<211> LENGTH: 20
<212> TYPE: DNA
<213> ORGANISM: Artificial Sequence
<220> FEATURE:
<221> NAME/KEY: primer_bind
<222> LOCATION: (1)...(20)
<223> OTHER INFORMATION: A80553 primer

<400> SEQUENCE: 26
ccccagcagc attgatgtcg                                                  20

<210> SEQ ID NO 27
<211> LENGTH: 1690
<212> TYPE: DNA
<213> ORGANISM: Homo sapiens

<400> SEQUENCE: 27
gtcacttagg aaaaggtgtc ctttcgggca gccgggctca gcatgaggaa cagaaggaat       60
gacactctgg acagcacccg gaccctgtac tccagcgcgt ctcggagcac agacttgtct      120
tacagtgaaa gcgacttggt gaattttatt caagcaaatt ttaagaaacg agaatgtgtc      180
ttctttacca agattccaa ggccacggag aatgtgtgca agtgtggcta tgcccagagc       240
cagcacatgg aaggcaccca gatcaaccaa agtgagaaat ggaactacaa gaaacacacc      300
aaggaatttc ctaccgacgc ctttgggat attcagtttg agacactggg gaagaaaggg      360
aagtatatac gtctgtcctg cgacacggac gcggaaatcc tttacgagct gctgacccag      420
cactggcacc tgaaaacacc caacctggtc atttctgtga ccgggggcgc caagaacttc     480
```

```
gccctgaagc cgcgcatgcg caagatcttc agccggctca tctacatcgc gcagtccaaa      540
ggtgcttgga ttctcacggg aggcacccat tatggcctga cgaagtacat cggggaggtg      600
gtgagagata acaccatcag caggagttca gaggagaata ttgtggccat ggcatagca       660 gcttggggca tggtctccaa ccgggacacc ctcatcagga attgcgatgc tgagggctat      720
tttttagccc agtaccttat ggatgacttc acaagggatc cactgtatat cctggacaac      780
aaccacacac atttgctgct cgtggacaat ggctgtcatg gacatcccac tgtcgaagca      840
aagctccgga atcagctaga aagcatatc tctgagcgca ctattcaaga ttccaactat       900
ggtggcaaga tccccattgt gtgttttgcc caaggaggtg aaaagagac tttgaaagcc       960 atcaatacct ccatcaaaaa taaaattcct tgtgtggtgg tggaaggctc gggccggatc     1020
gctgatgtga tcgctagcct ggtggaggtg aggatgccc cgacatcttc tgccgtcaag     1080
gagaagctgt gcgcttttt accccgcacg tgtcccggc tgtctgagga ggagactgag      1140
agttggatca aatggctcaa agaaattctc gaatgttctc acctattaac agttattaaa     1200
atggaagaag ctggggatga aattgtgagc aatgccatct cctacgctct atacaaagcc     1260
ttcagcacca gtgagcaaga caaggataac tggaatgggc agctgaagct tctgctggag     1320
tggaaccagc tggacttagc caatgatgag atttcacca atgaccgccg atgggagtct      1380
gctgaccttc aagaagtcat gtttacggct ctcataaagg acagacccaa gtttgtccgc     1440
ctctttctgg agaatggctt gaacctacgg aagtttctca cccatgatgt cctcactgaa     1500
ctcttctcca accacttcag cacgcttgtg taccggaatc tgcagatcgc caagaattcc     1560
tataatgatg ccctcctcac gtttgtctgg aaactggttg cgaacttccg aagaggcttc     1620
cggaaggaag acagaaatgg ccgggacgag atggacatag aactccacga cgtgtctcct     1680
attactcggc                                                             1690
```

<210> SEQ ID NO 28
<211> LENGTH: 3848
<212> TYPE: DNA
<213> ORGANISM: Homo sapiens

<400> SEQUENCE: 28

```
caaagtgaag aacgacatca atgctgctgg ggagtccgag gagctggcta atgagtacga       60
gacccgggct gttgagctgt tcactgagtg ttacagcagc gatgaagact ggcagaaca      120 gctgctggtc tattcctgtg aagcttgggg tggaagcaac tgtctggagc tggcggtgga      180
ggccacagac cagcatttca ccgcccagcc tgggtccag aattttcttt ctaagcaatg      240
gtatggagag atttcccgag acaccaagaa ctggaagatt atcctgtgtc tgtttattat      300
acccttggtg ggctgtggct ttgtatcatt taggaagaaa cctgtcgaca agcacaagaa      360
gctgctttgg tactatgtgg cgttcttcac ctcccccttc gtggtcttct cctggaatgt      420
ggtcttctac atcgccttcc tcctgctgtt tgcctacgtg ctgctcatgg atttccattc      480
ggtgccacac ccccccgagc tggtcctgta ctcgctggtc tttgtcctct ctgtgatga      540 agtgagacag tggtacgtaa atggggtgaa ttatttact gacctgtgga atgtgatgga      600
cacgctgggg cttttttact tcatagcagg aattgtattt cggctccact cttctaataa     660
aagctctttg tattctggac gagtcatttt ctgtctggac tacattattt tcactctaag     720
attgatccac attttactg taagcagaaa cttaggaccc aagattataa tgctgcagag     780
gatgctgatc gatgtgttct tcttcctgtt cctctttgcg gtgtggatgg tggcctttgg     840
```

-continued

```
cgtggccagg caagggatcc ttaggcagaa tgagcagcgc tggaggtgga tattccgttc      900
ggtcatctac gagccctacc tggccatgtt cggccaggtg cccagtgacg tggatggtac      960
cacgtatgac tttgcccact gcaccttcac tgggaatgag tccaagccac tgtgtgtgga     1020
gctggatgag cacaacctgc cccggttccc cgagtggatc accatccccc tggtgtgcat     1080
ctacatgtta tccaccaaca tcctgctggt caacctgctg gtcgccatgt ttggctacac     1140
ggtgggcacc gtccaggaga acaatgacca ggtctggaag ttccagaggt acttcctggt     1200
gcaggagtac tgcagccgcc tcaatatccc cttccccttc atcgtcttcg cttacttcta     1260
catggtggtg aagaagtgct tcaagtgttg ctgcaaggag aaaaacatgg agtcttctgt     1320
ctgctgtttc aaaaatgaag acaatgagac tctggcatgg gagggtgtca tgaaggaaaa     1380
ctaccttgtc aagatcaaca caaaagccaa cgacacctca gaggaaatga ggcatcgatt     1440
tagacaactg gatacaaagc ttaatgatct caagggtctt ctgaaagaga ttgctaataa     1500
aatcaaataa aactgtatga aactctaatg gagaaaaatc taattatagc aagatcatat     1560
taaggaatgc tgatgaacaa ttttgctatc gactactaaa tgagagattt tcagacccct     1620
gggtacatgg tggatgattt taaatcaccc tagtgtgctg agaccttgag aataaagtgt     1680
gtgattggtt tcatacttga agacggatat aaaggaagaa tatttccttt atgtgtttct     1740
ccagaatggt gcctgtttct ctctgtgtct caatgcctgg gactggaggt tgatagttta     1800
agtgtgttct taccgcctcc ttttcctttt aatcttattt ttgatgaaca catatatagg     1860
agaacatcta tcctatgaat aagaacctgg tcatgcttta ctcctgtatt gttattttgt     1920
tcatttccaa ttgattctct acttttccct tttttgtatt atgtgactaa ttagttggca     1980
tattgttaaa agtctctcaa attaggccag attctaaaac atgctgcagc aagaggaccc     2040
cgctctcttc aggaaaagtg ttttcatttc tcaggatgct tcttacctgt cagaggaggt     2100
gacaaggcag tctcttgctc tcttggactc accaggctcc tattgaagga accaccccca     2160
ttcctaaata tgtgaaaagt cgcccaaaat gcaaccttga aaggcactac tgactttgtt     2220
cttattggat actcctctta tttattattt ttccattaaa aataatagct ggctattata     2280
gaaaatttag accatacaga gatgtagaaa gaacataaat tgtccccatt accttaaggt     2340
aatcactgct aacaatttct ggatggtttt tcaagtctat tttttttcta tgtatgtctc     2400
aattctcttt caaaatttta cagaatgtta tcatactaca tatatacttt ttatgtaagc     2460
tttttcactt agtatttat caaatatgtt tttattatat tcatagcctt cttaaacatt     2520
atatcaataa ttgcataata ggcaacctct agcgattacc ataattttgc tcattgaagg     2580
ctatctccag ttgatcattg ggatgagcat cttttgtgcat gaatcctatt gctgtatttg     2640
ggaaattttt ccaaggttag attccaataa atatctattt attattaaat attaaaatat     2700
cgatttatta ttaaaaccat ttataaggct ttttcataaa tgtatagcaa ataggaatta     2760
ttaacttgag cataagatat gagatacatg aacctgaact attaaaataa atatattat      2820 ttaaccctag tttaagaaga agtcaatatg cttatttaaa tattatggat ggtgggcaga     2880
tcacttgagg tcaggagttc gagaccagcc tggccaacat ggcaaaacca catctctact     2940
aaaaataaaa aaattagctg ggtgtggtgg tgcactcctg taatcccagc tactcagaag     3000
gctgaggtac aagaattgct ggaacctggg aggcggaggt tgcagtgaac caagattgca     3060
ccactgcact ccagccgggg tgacagagtg agactccgac tgaaaataaa taataaata      3120 aataaataaa taaataaata aatattatgg atggtgaagg gaatggtata gaattggaga     3180
gattatctta ctgaacacct gtagtcccag cttctctctgg aagtggtggt atttgagcag     3240
```

```
gatgtgcaca aggcaattga aatgcccata attagtttct cagctttgaa tacactataa    3300
actcagtggc tgaaggagga aattttagaa ggaagctact aaaagatcta atttgaaaaa    3360
ctacaaaagc attaactaaa aaagtttatt ttccttttgt ctgggcagta gtgaaaataa    3420
ctactcacaa cattcactat gtttgcaagg aattaacaca aataaaagat gccttttac    3480 ttaaacgcca agacagaaaa cttgcccaat actgagaagc aacttgcatt agagagggaa    3540
ctgttaaatg ttttcaaccc agttcatctg gtggatgttt ttgcaggtta ctctgagaat    3600
tttgcttatg aaaaatcatt attttagtg tagttcacaa taatgtattg aacatacttc    3660
taatcaaagg tgctatgtcc ttgtgtatgg tactaaatgt gtcctgtgta cttttgcaca    3720
actgagaatc ctgcggcttg gtttaatgag tgtgttcatg aaataaataa tggaggaatt    3780
gtcaaaaaaa aaaaaaaaaa aaaaaaaaaa aaaaaaaaaa aaaaaaaaaa aaaaaaaaaa    3840
aaaaaaaa                                                            3848

<210> SEQ ID NO 29
<211> LENGTH: 342
<212> TYPE: DNA
<213> ORGANISM: Homo sapiens

<400> SEQUENCE: 29
cggaatctgc agatcgccaa gaattcctat aatgatgccc tcctcacgtt tgtctggaaa      60
ctggttgcga acttccgaag aggcttccgg aaggaagaca gaaatggccg ggacgagatg     120
gacatagaac tccacgacgt gtctcctatt actcggcacc ccctgcaagc tctcttcatc     180
tgggccattc ttcagaataa gaaggaactc tccaaagtca tttgggagca gaccaggggc     240
tgcactctgg cagccctggg agccagcaag cttctgaaga ctctggccaa agtgaagaac     300
gacatcaatg ctgctgggga gtccgaggag ctggctaatg ag                       342
```

PROSTATE TUMOR POLYNUCLEOTIDE COMPOSITIONS AND METHODS OF DETECTION THEREOF

This application claims the priority of U.S. Provisional Application No. 60/056,110 filed Aug. 20, 1997, which is incorporated herein by reference.

FIELD OF THE INVENTION

The invention relates to novel coding sequences and peptides derived from prostate tumors and to methods for detecting the presence of such tumor cells.

BACKGROUND OF THE INVENTION

Prostate carcinoma is a form of cancer that afflicts approximately 250,000 men in the United States each year, making it one of the most frequent cancers in Americans. It is also the second leading cause of cancer-related deaths in males in this country. While five-year survival rates for prostate carcinoma have generally improved over the past several decades, treatment for the advanced, metastatic form of the disease has not improved significantly.

Early detection and treatment of prostate cancer therefore remains one of the most effective measures to prevent further spread of and mortality from the disease. While a number of protein antigens have been discovered that are characteristic of malignant tumors, prostate tumors have not been particularly rich sources of target antigens that might be used for detection and/or immunotherapy of the disease, such as by passive immunotherapy.

It would therefore be useful to provide one or more disease-specific molecules or antigens that can be used in the early detection of prostate cancer. The present invention provides novel nucleotide sequences and corresponding expressed antigens that are useful in both the diagnosis and treatment of prostate carcinoma.

SUMMARY OF THE INVENTION

According to one aspect, the present invention is concerned with isolated nucleic acid molecules, which can be any form of RNA or DNA molecule that is useful, particularly in the area of diagnostic detection methods. The nucleic acid molecules described herein were identified on the basis of their unique presence in prostate tumor tissue samples. The molecules therefore have utility in detecting the presence, in a tissue or bodily fluid sample, of prostate tumor cells.

In one embodiment, the polynucleotides of the invention contain a region having sequence identity to a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8, and SEQ ID NO: 14, or is complementary to such encoding nucleic acid sequences.

In another embodiment, the polynucleotides of the invention will hybridize under high stringency conditions to a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8, and SEQ ID NO: 14, or the complement thereof.

Generally, according to a preferred aspect, the polynucleotide will be less than about 10 kilobases in length. In still a further aspect, the invention includes the recited polynucleotides. The invention also includes fragments of the polynucleotides of the present invention. In still another related aspect, the invention encompasses RNA molecules that are formed by translation of the foregoing nucleic acid sequences.

The isolated nucleic acid sequence may comprise the cDNA inserts of two pCR2.1 plasmid vectors (Invitrogen). The two clones which together make up the full-length SP 1–4 (SEQ ID NO: 14) sequence are designated pCR2.1/SP 1–4 (5' RACE, SEQ ID NO: 27) and pCR2.1/SP 1–4 (3' RACE, SEQ ID NO: 28). The approximate lengths of the plasmid inserts are 1.6 Kb and 4.0 Kb, respectively. The vectors deposited on Aug. 13, 1998 as ATCC 98827, 98828 and 98829 include the nucleotide sequences encoding SEQ ID NO: 15.

In another embodiment, the invention provides a vector comprising DNA encoding a prostate tumor antigen. A host cell comprising such a vector is also provided. By way of example, the host cells may be CHO cells, E. coli, insect cells or yeast. A process for producing prostate tumor antigens is further provided and comprises culturing host cells under conditions suitable for expression of a prostate tumor antigen and recovering the prostate tumor antigen from the cell culture.

Also useful and forming a part of the present invention are isolated nucleic acid molecules comprising DNA encoding prostate tumor antigens. In one aspect, the isolated nucleic acid comprises DNA encoding a prostate tumor antigen having an amino acid sequence selected from the group consisting of SEQ ID NOs: 9–11 and 15, or is complementary to such encoding nucleic acid sequences, and remains stably bound to it under at least moderate, and optionally, under high stringency conditions. Such peptides have utility in diagnostic assays, as well as in antigen compositions, such as peptide vaccines for use in eliciting humoral or cellular immune responses.

The invention further provides chimeric molecules comprising a prostate tumor antigen or extracellular domain thereof fused to a heterologous polypeptide or amino acid sequence. An example of such a chimeric molecule comprises a prostate tumor antigen fused to heterologous polypeptide which enhances the immunogenic properties of the antigen.

The invention also includes fragments of a prostate tumor antigen.

A further aspect of the invention is one or more antibodies which specifically bind to a prostate tumor antigen or an extracellular domain thereof. Optionally, the antibody is a monoclonal antibody. In still another aspect, the invention includes an antibody specific for a prostate tumor antigen. The antibody has diagnostic and therapeutic applications, particularly in treating prostate-related malignant disorders. Treatment methods include, but are not limited to, those which employ antisense or coding sequence polynucleotides for modulating the expression of prostate tumor antigen, as are treatment methods which employ antibodies specific for a prostate tumor antigen.

Diagnostic methods for detecting a prostate tumor antigen in specific tissue samples, and for detecting levels of expression of a prostate tumor antigen in tissues, also form part of the invention.

Furthermore, the polynucleotides recited above have particular utility in various nucleic acid-based detection assays Exemplary assays include in situ hybridization assays and PCR-based assays.

The invention also provides methods for diagnosing a prostate tumor-related condition in an individual. The presence of a prostate tumor antigen in a tissue from a first individual is measured and compared to a tissue from a second, unaffected individual. When a prostate tumor antigen is detected in said first individual and not in said second individual, the first individual is at risk for a prostate tumor related condition.

These and other objects and features of the invention will become more fully apparent when the following detailed description of the invention is read in conjunction with the accompanying drawings.

BRIEF DESCRIPTION OF THE FIGURES

FIG. 1 shows the sequence of a prostate-tumor derived polynucleotide of the invention, identified herein as SEQ ID NO: 1;

FIG. 2 shows the sequence of a prostate-tumor derived polynucleotide of the invention, identified herein as SEQ ID NO: 2;

FIG. 3 shows the sequence of a prostate-tumor derived polynucleotide of the invention, identified herein as SEQ ID NO: 3;

FIG. 4 shows the sequence of a prostate-tumor derived polynucleotide of the invention, identified herein as SEQ ID NO: 4;

FIG. 5 shows the sequence of a prostate-tumor derived polynucleotide of the invention, identified herein as SEQ ID NO: 5;

FIG. 6 shows the sequence of a prostate-tumor derived polynucleotide of the invention, identified herein as SEQ ID NO: 6;

FIG. 7 shows the sequence of a prostate-tumor derived polynucleotide of the invention, identified herein as SEQ ID NO: 7;

FIG. 8 shows the sequence of a prostate-tumor derived polynucleotide of the invention, identified herein as SEQ ID NO: 8;

FIGS. 9A–9C show the sequences of three peptides derived from SEQ ID NO: 5 as SEQ ID NO: 9 (9A), SEQ ID NO: 10 (9B) and SEQ ID NO: 11 (9C).

FIG. 10 shows the sequence of a prostate-tumor derived polynucleotide of the invention, identified herein as SEQ ID NO: 14, with the predicted 5' and 3' untranslated region depicted in lower case, the open reading frame from positions 43 to 3227 depicted in upper case, and the original partial cDNA fragment shown as underlined.

FIG. 11 shows the sequence of the polypeptide derived from SEQ ID NO: 14, identified as SEQ ID NO: 15.

DETAILED DESCRIPTION OF THE INVENTION

The present invention relates to novel nucleotide sequences that are unique to prostate tumors, as evidenced by preferential expression of such sequences in prostate tumor tissue samples. These sequences, including sequence variants and extended sequences thereof, have utility in diagnostic assays of body fluids or biopsied tissue to detect the presence of tumor cells. The proteins and peptides expressed by such DNA molecules are also encompassed by the present invention and may be used in diagnostic assays, as well as in developing pharmacologic strategies for disease intervention including immunotherapy, e.g. the use of antibodies that are specifically targeted to tumor cells.

I. Definitions

The term "polypeptide" as used herein refers to a compound made up of a single chain of amino acid residues linked by peptide bonds. The term "protein" as used herein may be synonymous with the term "polypeptide" or may refer, in addition, to a complex of two or more polypeptides.

Amino acid residues are referred to herein by their standard single letter notations: A, alanine; C, cysteine; D, aspartic acid; E, glutamic acid; F, phenylalanine; G, glycine; H, histidine; I, Isoleucine; K, lysine; L, leucine; M, methionine; N, asparagine; P, proline; Q, glutamine; R, arginine; S, serine; T, threonine; V, valine; W, tryptophan; Y, tyrosine.

The term "prostate tumor antigen" as used herein, encompasses native sequence prostate tumor antigens and polypeptide variants thereof. The prostate tumor antigen may be isolated from a variety of sources, such as from human tissue types or from another source, or prepared by recombinant or synthetic methods.

A "native sequence prostate tumor antigen" comprises a polypeptide having the same amino acid sequence as a prostate tumor antigen derived from nature. Such a native sequence prostate tumor antigen can be isolated from nature or can be produced by recombinant or synthetic means. The term "native sequence prostate tumor antigen" specifically encompasses naturally-occurring truncated or secreted forms of a prostate tumor antigen (e.g., soluble forms containing for instance, an extracellular domain sequence), naturally-occurring variant forms (e.g., alternatively spliced forms) and naturally-occurring allelic variants of a prostate tumor antigen.

"Percent (%) amino acid sequence identity" with respect to the amino acid sequences identified herein is defined as the percentage of amino acid residues in a candidate sequence that are identical with the amino acid residues in the native sequence, after aligning the sequences and introducing gaps, if necessary, to achieve the maximum percent sequence identity, and not considering any conservative substitutions as part of the sequence identity.

The term "polypeptide sequence variant" as used herein, refers to an active prostate tumor antigen having at least about 80% amino acid sequence identity with the prostate tumor antigen having the deduced amino acid sequences shown in FIGS. 9A–C and 11 (SEQ ID NOs:9–11 and 15, respectively) for a full-length native sequence prostate tumor antigen. Such prostate tumor antigen variants include, for instance, polypeptides wherein one or more amino acid residues are added, or deleted, at the N- or C-terminus of the sequence depicted in any one of FIGS. 9A–C and 11 (SEQ ID NOs: 9–11 and 15, respectively).

The term "fragment," when referring to a prostate tumor antigen, means a polypeptide which has an amino acid sequence which is the same as part of, but not all of, the amino acid sequence of the prostate tumor antigen which either retains essentially the same biological function or activity as the prostate tumor antigen, or retains at least one of the functions or activities of prostate tumor antigen; for example, a fragment which retains the ability to bind to a receptor, or a fragment which retains immunological activity of the prostate tumor antigen. The fragment preferably includes at least about 100–200 contiguous amino acid residues of the prostate tumor antigen, more preferably at least about 20–100 contiguous amino acid residues, even more more preferably at least about 10–20 contiguous amino acid residues, and most preferably at least about 9–10 contiguous amino acid residues of the prostate tumor antigen.

"Isolated", when used to describe the various polypeptides disclosed herein, means polypeptide that has been identified has also been separated and/or recovered from a component of its natural environment.

"Biologically active" or "biological activity" for the purposes herein refers to form(s) of prostate tumor antigen which retain the biologic and/or immunologic activities of the native or naturally-occurring prostate tumor antigen.

The term, "nucleic acid" as used herein refers to either DNA or RNA, or molecules which contain both deoxy-and ribonucleotides. The nucleic acids include genomic mRNA, DNA, cDNA, genomic DNA and oligonucleotides including sense and anti-sense nucleic acids. The term "nucleic acid" also includes fragments of the polynucleotides of the present invention, preferably at least about 300–600 nucleotides in length, more preferably about 150–300 nucleotides in length, even more more preferably about 30–150 nucleotides in length, and most preferably about 27–30 nucleotides in length. Such nucleic acids may also contain modifications in the ribose-phosphate backbone to increase stability and half life of such molecules in physiological environments.

The nucleic acid may be double stranded, single stranded, or contain portions of both double stranded or single stranded sequence. The depiction of a single strand also defines the sequence of the other strand and thus also includes the complement of the sequence.

The term "polynucleotide" as used herein refers to a polymeric molecule having a backbone that supports bases capable of hydrogen bonding to typical polynucleotides, where the polymer backbone presents the bases in a manner to permit such hydrogen bonding in a sequence specific fashion between the polymeric molecule and a typical polynucleotide (e.g., single-stranded DNA). Such bases are typically inosine, adenosine, guanosine, cytosine, uracil and thymidine. Polymeric molecules include double and single stranded ribonucleic acids (RNA) and deoxyribonucleic acids (DNA), and may include polymers having backbone modifications such methylphosphonate linkages.

The term, "recombinant nucleic acid" as used herein refers to nucleic acid, originally formed in vitro, in general, by the manipulation of nucleic acid by endonucleases, in a form not normally found in nature.

Nucleic acid subunits are referred to herein by their standard base designations; T, thymine; A, adenosine; C, cytosine; G, guanine, U, uracil; variable positions are referred to by standard IUPAC abbreviations: W, A or T/U; R, A or G; S, C or G; K: G or T/U (37 CFR. §1.822).

"Percent (%) nucleic acid sequence identity" with respect to the prostate tumor antigen sequence identified herein is defined as the percentage of nucleotides in a candidate sequence that are identical with the nucleotides in the disclosed prostate tumor antigen sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as ALIGN or Megalign (DNASTAR) software. Those skilled in the art can determine appropriate parameters for measuring alignment, including any algorithms needed to achieve maximal alignment over the length of the sequences being compared.

The term "vector" refers to a nucleotide sequence that can assimilate new nucleic acids, and propagate those new sequences in an appropriate host. Vectors include, but are not limited to recombinant plasmids and viruses. The vector (e.g., plasmid or recombinant virus) comprising the nucleic acid of the invention can be in a carrier, for example, a plasmid complexed to a protein, a plasmid complexed with lipid-based nucleic acid transduction systems, or other non-viral carrier systems.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

The terms "polymerase chain reaction" and "PCR" refer to a process of amplifying one or more specific nucleic acid sequences, wherein (i) oligonucleotide primers which determine the ends of the sequences to be amplified are annealed to single-stranded nucleic acids in a test sample, (ii) a nucleic acid polymerase extends the 3' ends of the annealed primers to create a nucleic acid strand complementary in sequence to the nucleic acid to which the primers were annealed, (iii) the resulting double-stranded nucleic acid is denatured to yield two single-stranded nucleic acids, and (iv) the processes of primer annealing, primer extension, and product denaturation are repeated enough times to generate easily identified and measured amounts of the sequences defined by the primers. The sequential annealing, extension and denaturation steps are controlled by varying the temperature of the reaction container, normally in a repeating cyclical manner. Annealing and extension are typically carried out between 40–80% C., whereas denaturation requires temperatures between about 80 and 100% C. A "thermal cycler", such as Perkin Elmer Model 9600, is typically used to regulate the reactions.

The term "antibody" is used in the broadest sense and specifically covers single anti-prostate tumor antigen monoclonal antibodies (including agonist, antagonist, and neutralizing antibodies) and anti-prostate tumor antigen antibody compositions with polyepitopic specificity.

The term "monoclonal antibody" as used herein refers to an antibody obtained from a population of substantially homogeneous antibodies, i.e., the individual antibodies comprising the population are identical except for possible naturally-occurring mutations that may be present in minor amounts.

II. Identification of Prostate Tumor-Specific DNA Molecules

Prostate cancer-specific genes can be isolated by a various techniques known to those of skill in the art that allow for detection of differences in gene expression between two or more sources of nucleic acid, e.g. differential expression in response to temporal development, disease and/or mitogenic stimulus.

An "isolated" prostate tumor antigen-encoding nucleic acid is a nucleic acid molecule that is identified and separated from at least one contaminant with which it is ordinarily associated. An isolated prostate tumor antigen-encoding nucleic acid is other than in the form or setting in which it is found in nature and is therefore distinguished from such prostate tumor antigen-encoding nucleic acids as they exist in natural cells.

Using differential display or various subtractive hybridization strategies, mRNA derived from related cell types can be compared to provide qualitative and quantitative differences in specific mRNA species.

Differential display (DD) uses two different types of primers to convert different fractions of the mRNA pool constituency into double-stranded cDNA fragments. These fragments are separated electrophoretically to provide an expression profile "bar code." The first primer is generically referred to as the "anchored" primer. Most anchored primers use a group of 10–12 dTs to achieve annealing with the poly(A+) tail of the mRNAs. First strand cDNA synthesis occurs off the anchored primer, thereby anchoring to the 3' end of the transcript. Anchored primers employ either one or two non-dt bases to achieve annealing of the anchored primer to a subset of mRNAs within the mRNA pool. Single-base anchored primers generate three different fractions, corresponding to the presence of either a C, G or T immediately upstream of the poly(A+) region. Assuming 10,000–15,000 different species of mRNA present, each single-base anchored primer is expected to generate approximately 3,000–5,000 different first-strand cDNAs. There are twelve different two-base pair combinations possible immediately upstream of the poly(A+) region, with each representing a considerably smaller subset of the mRNA pool than single-base permutations. Each two-base anchored primer theoretically selects approximately 1/12 (8%) of the mRNA pool constituency, or approximately 800–1,200 different first-strand cDNAs. Anchored primers employing two non-dt bases to 'cull' the mRNA pool provide a more manageable number of cDNA fragments.

After first strand synthesis is complete, aliquots of the reactions are subjected to exponential (bi-directional) polymerase chain reaction (PCR) amplification using the original anchored primer in combination with a second, upstream or "arbitrary" primer. Arbitrary primers contain sequences that are designed to anneal at sites upstream of the anchored primer, converting the first-strand cDNA into one or more truncated cDNA fragments. The RNA samples to be compared serve as templates for first-strand cDNA synthesis in reverse transcription reactions using a set of 12 different oligo(dT) anchored 3' primers. The cDNAs produced in the RT reactions are then used in duplicate DD-PCR reactions using the same anchored 3' primers used in the RT reactions, in pairwise combinations with four different arbitrary 5' primers. Each RNA sample is amplified by 48 primer pair combinations. The duplicate DD-PCR samples are loaded on adjacent lanes of a high resolution denaturing gel, with samples from different RNAs amplified with the same anchored and arbitrary primer pairs, grouped together in consecutive lanes. Gels are subjected to autoradiography, and bands that appear in the prostate tumor-derived samples, but not in control samples (such as in normal prostate tissue or HeLa cell samples) are selected for further processing. Example 1 provides details of the experimental procedures used in experiments carried out in support of the present invention.

As described in Example 1, when RNA from prostate tumor derived tissue was compared to RNA from normal prostate tissue or HeLa cell samples, 54 unique DD products were identified. The corresponding bands were excised from the gels, reamplified by PCR, gel purified and 5' ends were subjected to DNA sequencing by cycle sequencing.

Subtractive hybridization, followed by one or more rounds of PCR amplification of the sequences obtained following subtraction, is useful to isolate nucleic acids that are preferentially expressed, e.g. in disease state, but not in normal, healthy tissue or in one tissue type and not in another.

As described in Example 3A–B, a prostate tumor specific partial cDNA sequence was identified using a subtractive hybridization strategy and PCR amplification, with the corresponding full length sequence identified by rapid amplification of cDNA ends [RACE, Frohman et al., *Proc. Nat. Acad. Sci.* 85:8998–9002 (1988)], using a single gene-specific oligonucleotide primer.

The sequences were compared to published databanks, as discussed in Example 2, and eight novel mRNAs/CDNAs presented herein as SEQ ID NOs: 1–4, and 6–8 were obtained by the differential display method with an additional sequence designated SP 1–4 (SEQ ID NO: 14), obtained by subtractive hybridization. One of the sequences obtained by the differential display method, SEQ ID NO: 5, was further found to have some degree of homology to thioredoxin reductase, according to methods detailed in Example 2.

A. Identification of Prostate Tumor-Specific DNA Sequence Variants and Peptides

The present invention encompasses, in addition to DNA molecules having the specific sequences recited herein, sequence variants, extended sequences and peptides derived from such sequences. This section describes how these various molecules are identified in accordance with the present invention.

1. DNA Sequence Variants.

a. Sequence Identity and Specific Hybridization. A "variant" polynucleotide sequence encodes a "variant" amino acid sequence which is altered by one or more amino acids from the reference polypeptide sequence.

Sequence variants include polynucleotide sequences that have at least about 80% nucleic acid sequence identity, preferably at least about 85% nucleic acid sequence identity, more preferably at least about 90% nucleic acid sequence identity and even more preferably at least about 95–98% nucleic acid sequence identity with the nucleic acid sequence of any one of SEQ ID NOs: 1–8 and 14, respectively.

Sequence identity in the context of a nucleic acid which encodes a prostate tumor antigen means identical nucleic acids at corresponding positions in the two sequences which are being compared. Sequence comparison are carried out using standard techniques known in the art, as detailed below.

A functional measure of sequence identity that may alternatively be used to assess similarity of sequences is the ability of a particular nucleotide molecule to hybridize with a second nucleotide under defined conditions. "Hybridization" includes any process by which a strand of a nucleic acid joins with a complementary strand through base-pairing. Thus, strictly speaking, the term refers to the ability of the complement of the test sequence to bind to the test sequence, or vice-versa.

The nucleic acid similarity may be determined through hybridization studies. Thus, for example, nucleic acids which hybridize under high stringency to the nucleic acid sequences shown in FIGS. 1–8 and 14, or the complement thereof, are considered a prostate tumor antigen gene. High stringency conditions are known in the art; an example of such conditions includes hybridization at about 65° C. in about 5×SSPE and washing conditions of about 65° C. in about 0.1×SSPE. See Maniatis, et al., *MOLECULAR CLONING: A LABORATORY MANUAL*, 2d Edition (1989), and Ausubel, F. M., et al., Eds., *CURRENT PROTOCOLS IN MOLECULAR BIOLOGY*, John Wiley & Sons, Inc., Copyright (c)1987, 1988, 1989, 1990 by Current Protocols, both of which are hereby incorporated by reference.

Hybridization conditions are based on the melting temperature (Tm) of the nucleic acid binding complex or probe and are typically classified by degree of "stringency" of the conditions under which hybridization is measured. (Ausubel, et al., 1990) For example, "maximum stringency" typically occurs at about Tm-5% C. (5% below the Tm of the probe); "high stringency" at about 5–10% below the Tm; "intermediate stringency" at about 10–20% below the Tm of the probe; and "low stringency" at about 20–25% below the Tm. Functionally, maximum stringency conditions may be used to identify sequences having strict identity or near-strict identity with the hybridization probe; while high stringency conditions are used to identify sequences having about 80% or more sequence identity with the probe.

2. Degeneracy of Genetic Code. Sequence variants also include nucleic acid molecules that encode the same peptide as is encoded by the tumor specific nucleic acid molecules described herein. Thus, where the coding frame of the various identified nucleic acid molecules is known, for example by homology to known genes or by extension of the sequence, as described in Parts B or C below, it is appreciated that as a result of the degeneracy of the genetic code, a number of coding sequences can be produced. For example, the triplet CGT encodes the amino acid arginine. Arginine is alternatively encoded by CGA, CGC, CGG, AGA, and AGG. Therefore it is appreciated that such substitutions in the coding region fall within the sequence variants that are covered by the present invention. Any and all of these sequence variants can be utilized in the same ways as are described herein for the identified parent sequences SEQ ID NOs: 1–8.

It is further appreciated that such sequence variants may or may not hybridize to the parent sequence under conditions of high stringency. This would be possible, for example, when the sequence variant includes a different codon for each of the amino acids encoded by the parent nucleotide. Such variants are, nonetheless, specifically contemplated and encompassed by the present invention. In accordance with the present invention, also encompassed are sequences that at least 80% identical to such degeneracy-derived sequence variants.

Although nucleotide sequence variants are preferably capable of hybridizing to the nucleotide sequences recited herein under conditions of moderately high or high stringency, there are, in some situations, advantages to using variants based on the degeneracy of the code, as described above. For example, codons may be selected to increase the rate at which expression of the peptide occurs in a particular procaryotic or eukaryotic organism, in accordance with the optimum codon usage dictated by the particular host organism. Alternatively, it may be desirable to produce RNA having longer half lives than the mRNA produced by the recited sequences.

3. Extended Polynucleotide Sequences. Polynucleotide sequences recited herein may be extended using various methods known in the art to detect upstream sequences such as promoters and regulatory elements. For example, "restriction site" polymerase chain reaction is a direct method which uses universal primers to retrieve unknown sequences adjacent to a known sequence. First, a genomic DNA is amplified in the presence of a primer directed to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Likewise, a method known as "inverse PCR" can be used to amplify or extend sequences using divergent primers based on a known region. The primers may be designed using standard primer analysis software, for example Gene-Works (Oxford Biomolecular Systems, CA) to be at least 15 nt in length, with a GC content of 50% or more and to anneal to the target sequence at temperatures about 68–72%. The method requires the use of several restriction enzymes to generate a suitable fragment in the known region of a gene. The fragment is then circularized by ligation and is used as a PCR template. Alternatively, adjacent and full length sequences, and particularly, intron/exon junctions, may be identified using a kit such as "PROMOTER-FINDER" (Clontech Labs, Palo Alto, Calif.). This kit uses PCR, nested primers and specific libraries to walk in genomic DNA.

Preferred libraries for screening for full-length cDNAs are ones that have been size-selected to include larger cDNAs. Random primed libraries are preferred since they contain more sequences which include the 5' and upstream regions of genes. Genomic libraries are useful for extension into the 5' nontranslated regulatory region. Preferably, such libraries will be generated from the tumor cells of interest, such as the prostate tumor cells exemplified herein.

Analysis of the size and sequence of full length sequences identified in accordance with the present invention may be carried out by standard methods known in the art, such as automated sequencing methods, gel size analysis and capillary electrophoresis.

Where the full length sequence is identified, it will be appreciated that additional regions of the full length sequence may be used to make hybridization probes and/or tumor detection reagents in accordance with the present invention. Specifically, knowledge of a partial or full-length sequence makes possible searches of widely available databases, in order to determine whether the subject sequence may have homologies in other species or tissues, particularly tumor tissues. Examples of homologies based on the current sequences are presented in Example 2, herein.

The full length sequence can also be used to construct a recombinant nucleic inserted into a vector and used to express the encoded polypeptide, as discussed in Part D, below.

It is understood that once a recombinant nucleic acid is made and reintroduced into a host cell or organism, it will replicate non-recombinantly, using the cellular machinery of the host cell, and such nucleic acids, once produced recombinantly, although subsequently replicated non-recombinantly, are still considered recombinant for the purposes of the invention.

4. Polypeptide Variants. In one embodiment of the invention, the native sequence prostate tumor antigen is a mature or full-length native sequence prostate tumor antigen comprising amino acids 1 to 1095 of FIG. 11 (SEQ ID NO: 15). In another embodiment of the invention, the native sequence prostate tumor antigen is an extracellular domain of the full-length prostate tumor antigen. Optionally, the prostate tumor antigen is obtained or obtainable by expressing the polypeptide encoded by the cDNA insert of the vectors pCR2.1/SP 1–4 (5' RACE, SEQ ID NO: 27) and pCR2.1/SP 1–4 (3' RACE, SEQ ID NO: 28) have been deposited with ATCC and are assigned ATCC deposit numbers 98827, 98828, and 98829, respectively.

Ordinarily, a prostate tumor antigen variant will have at least about 80% amino acid sequence identity, preferably at least about 85% amino acid sequence identity, more preferably at least about 90% amino acid sequence identity and even more preferably at least about 95–98% amino acid sequence identity with the amino acid sequence depicted in any one of FIGS. 9A–C and 11 (SEQ ID NOs: 9–11 and 15, respectively).

Sequence similarity in the context of a prostate tumor antigen means sequence similarity or identity, with identity being preferred. Identical in this context means identical amino acids at corresponding positions in the two sequences which are being compared. Similarity in this context includes amino acids which are identical and those which are similar (functionally equivalent). This similarity or identity will be determined using standard techniques known in the art, for example, the "Best Fit" sequence program described by Devereux, et al., *Nucl. Acid Res.* 12:387–395 (1984), the BLASTP or BLASTX program [Altshul et al., *Methods in Enzymology* 266:460–480 (1990), *Nucl. Acids Res.* 25:3389–3402 (1997)], preferably using the default settings. The alignment may include the introduction of gaps in the sequences to be aligned. In addition, for sequences which contain either more or fewer amino acids than the relevant native protein, it is understood that the percentage of similarity will be determined based on the number of similar or identical amino acids in relation to the total number of amino acids. Alignment for purposes of determining percent amino acid sequence identity can be achieved in various ways that are within the skill in the art, for instance, using publicly available computer software such as LALIGN or Megalign (DNASTAR) software with default parameters. The LALIGN program is found in the FASTA version 1.7 suite of sequence comparison programs (Pearson, et al., 1988; Pearson, 1990; program available from William R. Pearson, Department of Biological Chemistry, Box 440, Jordan Hall, Charlottesville, Va.).

Those skilled in the art can determine appropriate parameters for measuring alignment, including selecting an algorithm (e.g. "Best Fit" or "BLASTX") needed to achieve maximal alignment over the sequences being compared [see also, Pearson, et al., *Methods in Enzymol.* 266:227–258 (1996)]. An exemplary alignment may be carried out using the LALIGN program found in the FASTA Version 2.0 suit of programs with default parameters which include the Smith-Waterman algorithm, the BLOSUM50 matrix, a ktup of 2 and a gap penalty of −12/−2.

Also included within the definition of prostate tumor antigens of the present invention are amino acid sequence variants. These variants fall into one or more of three classes: substitutional, insertional or deletional variants. These variants ordinarily are prepared by site specific mutagenesis of nucleotides in the DNA encoding the prostate tumor antigen, using cassette or PCR mutagenesis or other techniques well known in the art, to produce DNA encoding the variant, and thereafter expressing the DNA in recombinant cell culture. However, variant prostate tumor antigen fragments having up to about 100–150 residues may be prepared by in vitro synthesis using established techniques. Amino acid sequence variants are characterized by the predetermined nature of the variation, a feature that sets them apart from naturally occurring allelic or interspecies variation of the prostate tumor antigen amino acid sequence. The variants typically exhibit the same qualitative biological activity as the naturally occurring analogue, although variants can also be selected which have modified characteristics as will be more fully outlined below.

A "substitution" results from the replacement of one or more nucleotides or amino acids by different nucleotides or amino acids, respectively.

An "insertion" or "addition" is that change in a nucleotide or amino acid sequence which has resulted in the addition of one or more nucleotides or amino acid residues, respectively, as compared to the naturally occurring sequence.

A "deletion" is defined as a change in either nucleotide or amino acid sequence in which one or more nucleotides or amino acid residues, respectively, are absent.

While the site or region for introducing an amino acid sequence variation is predetermined, the change per se need not be predetermined. For example, in order to optimize the performance of a mutation at a given site, random mutagenesis may be conducted at the target codon or region and the expressed prostate tumor antigen variants screened for the optimal combination of desired activity. Techniques for making substitutions at predetermined sites in DNA having a known sequence are well known, for example, M13 primer mutagenesis and PCR mutagenesis. Screening of the mutants may be done directly by PCR, or following expression of the modified sequence using assays for prostate tumor antigen, for example, antibody detection studies may be done.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances.

Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids.

The variation allowed with retention of biological activity may be determined by systematically making insertions, deletions or substitutions of amino acids in the sequence and testing the resulting variants for activity. Gene expression, may be measured by immunological methods, such as immunohistochemical staining of cells or tissue sections and assay of cell culture or body fluids, to quantitate directly the expression of the gene product. Antibodies useful for immunohistochemical staining and/or assay of sample tissues or fluids may be either monoclonal or polyclonal, and may be prepared against a native prostate tumor antigen, a synthetic peptide based on the DNA sequences provided herein or against a heterologous fusion protein which includes a prostate tumor specific antibody epitope. Examples prostate cancer antigens with diagnostic utility in antibody-based assays include, but are not limited to, prostate-specific antigen (PSA, U.S. Pat. Nos. 5,710,007; 5,614,372; 5,672,480 and others), prostate-specific membrane antigen (PSMA, U.S. Pat. No. 5,538,866) and human prostatic glandular kallikrein (HK-2, U.S. Pat. No. 5,516,639). Many diagnostic assays based on various different technologies routinely used by those of skill in the art have been developed for these molecules.

When small alterations in the characteristics of the prostate tumor antigen are desired, substitutions are generally made in accordance with known "conservative substitutions".

A "conservative substitution" refers to the substitution of an amino acid in one class by an amino acid in the same class, where a class is defined by common physicochemical amino acid side chain properties and high substitution frequencies in homologous proteins found in nature (as determined, e.g., by a standard Dayhoff frequency exchange matrix or BLOSUM matrix). Six general classes of amino acid side chains, categorized as described above, include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution.

A "non-conservative substitution" refers to the substitution of an amino acid in one class with an amino acid from another class; for example, substitution of an Ala, a class II residue, with a class III residue such as Asp, Asn, Glu, or Gln.

Substantial changes in function or immunological identity are made by selecting substitutions that are "non-conservative substitutions". For example, substitutions may be made which more significantly affect; the structure of the polypeptide backbone in the area of the alteration, for example the alpha-helical or beta-sheet structure, the charge or hydrophobicity of the molecule at the target site, or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

Prostate tumor antigen variants typically exhibit the same qualitative biological activity and will elicit the same immune response as the naturally-occurring analogue, although variants also are selected to modify the characteristics of the prostate tumor antigen, as needed. For example, glycosylation sites, and more particularly one or more O-linked or N-linked glycosylation sites may be altered or removed. Those skilled in the art will appreciate that amino acid changes may alter post-translational processes of the prostate tumor antigen, such as changing the number or position of glycosylation sites or altering the membrane anchoring characteristics.

The variations can be made using methods known in the art such as oligonucleotide-mediated (site-directed) mutagenesis, alanine scanning, and PCR mutagenesis. Site-directed mutagenesis [Carter et al., *Nucl. Acids Res.* 13:4331 (1986); Zoller et al., *Nucl. Acids Res.* 10:6487 (1987)], cassette mutagenesis [Wells et al., *Gene* 34:315 (1985)], restriction selection mutagenesis [Wells et al., *Philos. Trans. R. Soc. London SerA* 317:415 (1986)] or other known techniques can be performed on the cloned DNA to produce the prostate tumor antigen-encoding variant DNA.

Also included with the definition of prostate tumor antigen proteins are other related prostate tumor antigen proteins. Thus, probe or degenerate polymerase chain reaction (PCR) primer sequences may be used to find other related proteins. Useful probe or primer sequences may be designed to: all or part of the prostate tumor antigen sequence, or sequences outside the coding region. As is generally known in the art, preferred PCR primers are from about 15 to about 35 nucleotides in length, with from about 20 to about 30 being preferred, and may contain inosine as needed. The conditions for the PCR reaction are generally known in the art.

B. Modifications of Prostate Tumor Antigens

Covalent modifications of a prostate tumor antigen are included within the scope of this invention. One type of covalent modification includes reacting targeted amino acid residues of a prostate tumor antigen with an organic derivatizing agent that is capable of reacting with selected side chains or the N- or C-terminal residues of a prostate tumor antigen polypeptide. Derivatization with bifunctional agents is useful, for instance, for crosslinking a prostate tumor antigen to a water-insoluble support matrix or surface. Commonly used crosslinking agents include, e.g., 1,1-bis(diazo acetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio] propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *PROTEINS: STRUCTURE AND MOLECULAR PROPERTIES*, W. H. Freeman & Co., San Francisco, pp. 79–86 (1983)], acetylation of the N-terminal amine, and amidation of any C-terminal carboxyl group.

Another type of covalent modification of a prostate tumor antigen polypeptide included within the scope of this invention comprises altering the native glycosylation pattern of the polypeptide, namely modifying a native sequence prostate tumor antigen polypeptide by deleting one or more carbohydrate moieties from and/or adding one or more carbohydrate moieties to, the native sequence prostate tumor antigen polypeptide.

Addition of glycosylation sites to a prostate tumor antigen polypeptides may be accomplished by altering the amino acid sequence thereof. The alteration may be made, for example, by the addition of, or substitution by, one or more serine or threonine residues to the native sequence prostate tumor antigen polypeptide (for O-linked glycosylation sites). The prostate tumor antigen amino acid sequence may optionally be altered through changes at the DNA level, particularly by mutating the DNA encoding the prostate tumor antigen polypeptide at preselected bases such that codons are generated that will translate into the desired amino acids.

Another means of increasing the number of carbohydrate moieties on the prostate tumor antigen polypeptide is by chemical or enzymatic coupling of glycosides to the polypeptide. Such methods are described in the art, e.g., in WO 87/05330 published Sept. 11, 1987, and in Aplin and Wriston, *CRC Crit. Rev. Biochem.*, pp. 259–306 (1981).

Removal of carbohydrate moieties present on the prostate tumor antigen polypeptide may be accomplished chemically or enzymatically or by mutational substitution of codons encoding for amino acid residues that serve as targets for glycosylation. In addition, carbohydrate moieties may be removed by enzymatic cleavage by the use of a variety of endo-and exo-glycosidases as described by Thotakura, et al., *Meth. Enzymol.* 138:350 (1987) or by chemical deglycosylation techniques described, for example, in Hakimuddin, et al., *Arch. Biochem. Biophys.* 259:52 (1987) and by Edge, et al., *Anal. Biochem.* 118:131 (1981).

Another type of covalent modification of a prostate tumor antigen comprises linking the antigen to a non proteinaceous polymer, e.g., polyethylene glycol, polypropylene glycol, or polyoxyalkylenes, for example, as set forth in U.S. Pat. No. 4,791,192.

C. Encoded Polypeptide Antigens

1. Expression of Prostate Tumor Antigens. The polynucleotide sequences described herein can be used in recombinant DNA molecules that direct the expression of the corresponding polypeptides in appropriate host cells. As discussed above, genetic code degeneracy dictates that other DNA sequences which encode substantially the same or a functionally equivalent amino acid sequence may be used to clone and express the identified polypeptides. Codons preferred by a particular host cell may be selected and substituted into the naturally occurring nucleotide sequences, to increase the rate and/or efficiency of expression.

The nucleic acid (e.g., cDNA or genomic DNA) encoding the desired prostate tumor antigen polypeptide may be inserted into a replicable vector for cloning (amplification of the DNA), or for expression. The polypeptide can be expressed recombinantly in any of a number of expression systems according to methods known in the art (Ausubel, et al., 1990).

Appropriate host cells include yeast, bacteria, archebacteria, fungi, and insect and animal cells, including mammalian cells, for example primary cells, including stem cells, including, but not limited to bone marrow stem cells. More specifically, these include, but are not limited to, microorganisms such as bacteria transformed with recombinant bacteriophage, plasmid or cosmid DNA expression vectors, and yeast transformed with yeast expression vectors. Also included, are insect cells infected with a recombinant insect virus (such as baculovirus), and mammalian expression systems.

The nucleic acid sequence to be expressed may be inserted into the vector by a variety of procedures. In general, DNA is inserted into an appropriate restriction endonuclease site using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The prostate tumor antigen proteins of the present invention are produced by culturing a host cell transformed with an expression vector containing a nucleic acid encoding a prostate tumor antigen protein, under the appropriate conditions to induce or cause expression of the protein. The conditions appropriate for prostate tumor antigen protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

A host cell strain may be chosen for its ability to modulate the expression of the inserted sequences or to process the expressed protein in the desired fashion. Such modifications of the protein include, but are not limited to, acetylation, carboxylation, glycosylation, phosphorylation, lipidation and acylation. Post-translational processing which cleaves a "prepro" form of the protein may also be important for correct insertion, folding and/or function. By way of example, host cells such as CHO, HeLa, BHK, MDCK, 293, W138, etc. have specific cellular machinery and characteristic mechanisms for such post-translational activities and may be chosen to ensure the correct modification and processing of the introduced, foreign protein. Of particular interest are *Drosophila melangaster* cells, *Saccharomyces cerevisiae* and other yeasts, *E. coli, Bacillus subtilis,* SF9 cells, C129 cells, 293 cells, Neurospora, BHK, CHO, COS, and HeLa cells, fibroblasts, Schwanoma cell lines, immortalized mammalian myeloid and lymphoid cell lines, Jukat cells, human cells and other primary cells.

The nucleic acid must be "operably linked" by placing it into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" DNA sequences are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Promoter sequences encode either constitutive or inducible promoters. The promoters may be either naturally occurring promoters or hybrid promoters. Hybrid promoters, which combine elements of more than one promoter, are also known in the art, and are useful in the present invention.

The expression vector may comprise additional elements, for example, the expression vector may have two replication systems, thus allowing it to be maintained in two organisms, for example in mammalian or insect cells for expression and in a procaryotic host for cloning and amplification.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2: plasmid origin is suitable for yeast, and various viral origins (SV40, polyoma, adenovirus, VSV or BPV) are useful for cloning vectors in mammalian cells.

Further, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

Preferably, the expression vector contains a selectable marker gene to allow the selection of transformed host cells. Selection genes are well known in the art and will vary with the host cell used.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

Host cells transformed with a nucleotide sequence encoding a prostate tumor antigen may be cultured under conditions suitable for the expression and recovery of the encoded protein from cell culture. The protein produced by a recombinant cell may be secreted, membrane-bound, or contained intracellularly depending on the sequence and/or the vector used. As will be understood by those of skill in the art, expression vectors containing polynucleotides encoding the prostate tumor antigen can be designed with signal sequences which direct secretion of the prostate tumor antigen through a prokaryotic or eukaryotic cell membrane.

The desired prostate tumor antigen polypeptide may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the prostate tumor antigen-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including Saccharomyces and Kluyveromyces α-factor leaders, the latter described in U.S. Pat. No. 5,010,182), or acid phosphatase leader, the *C. albicans* glucoamylase leader (EP 362,179 published Apr. 4, 1990), or the signal described in WO 90/13646 published Nov. 15, 1990. In mammalian cell expression, mammalian signal sequences may be used to direct secretion of the protein, such as signal sequences from secreted polypeptides of the same or related species, as well as viral secretory leaders.

According to the expression system selected, the coding sequence is inserted into an appropriate vector, which in turn may require the presence of certain characteristic "control elements" or "regulatory sequences." Appropriate constructs are known generally in the art (Ausubel, et al., 1990) and, in many cases, are available from commercial suppliers such as Invitrogen (San Diego, Calif.), Stratagene (La Jolla, Calif.), Gibco BRL (Rockville, Md.) or Clontech (Palo Alto, Calif.).

a. Expression in Bacterial Systems. Transformation of bacterial cells may be achieved using an inducible promoter such as the hybrid lacZ promoter of the "BLUESCRIPT" Phagemid (Stratagene) or "pSPORT1" (Gibco BRL). In addition, a number of expression vectors may be selected for use in bacterial cells to produce cleavable fusion proteins that can be easily detected and/or purified, including, but not limited to "BLUESCRIPT" (α-galactosidase; Stratagene) or pGEX (glutathione S-transferase; Promega, Madison, Wis.).

A suitable bacterial promoter is any nucleic acid sequence capable of binding bacterial RNA polymerase and initiating the downstream (3') transcription of the coding sequence of the prostate tumor antigen gene into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences.

Furthermore, a bacterial promoter can include naturally occurring promoters of non-bacterial origin that have the ability to bind bacterial RNA polymerase and initiate transcription. An efficient ribosome binding site is also desirable.

The expression vector may also include a signal peptide sequence that provides for secretion of the prostate tumor antigen protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria). The bacterial expression vector may also include a selectable marker gene to allow for the selection of bacterial strains that have been transformed. Suitable selection genes include drug resistance genes such as ampicillin, chloramphenicol, erythromycin, kanamycin, neomycin and tetracycline. Selectable markers also include biosynthetic genes, such as those in the histidine, tryptophan and leucine biosynthetic pathways.

When large quantities of prostate tumor antigen are needed, e.g., for the induction of antibodies, vectors which direct high level expression of fusion proteins that are readily purified may be desirable. Such vectors include, but are not limited to, multifunctional *E. coli* cloning and expression vectors such as BLUESCRIPT(R) (Stratagene), in which the prostate tumor antigen coding sequence may be ligated into the vector in-frame with sequences for the amino-terminal Met and the subsequent 7 residues of beta-galactosidase so that a hybrid protein is produced; pIN vectors [Van Heeke & Schuster *J Biol Chem* 264:5503–5509 1989)]; pET vectors (Novagen, Madison Wis.); and the like.

Expression vectors for bacteria include the various components set forth above, and are well known in the art. Examples include vectors for *Bacillus subtilis, E. coli, Streptococcus cremoris,* and *Streptococcus lividans,* among others. Bacterial expression vectors are transformed into bacterial host cells using techniques well known in the art, such as calcium chloride mediated transfection, electroporation, and others.

b. Expression in Yeast. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe,* and *Yarrowia lipolytica.* Examples of suitable promoters for use in yeast hosts include the promoters for 3-phosphoglycerate kinase [Hitzeman et al., *J. Biol. Chem.* 255:2073 (1980)] or other glycolytic enzymes [Hess et al., *J. Adv. Enzyme Reg.* 7:149 (1968); Holland, *Biochemistry* 17:4900 (1978)], such as enolase, glyceraldehyde-3-phosphate dehydrogenase, hexokinase, pyruvate decarboxylase, phosphofructokinase, glucose- 6-phosphate isomerase, 3-phosphoglycerate mutase, pyruvate kinase, triosephosphate isomerase, phosphoglucose isomerase, alpha factor, the ADH2/GAPDH promoter, glucokinase alcohol oxidase, and PGH. [See, for example, Ausubel, et al., 1990; Grant et al., *Methods in Enzymology* 153:516–544, (1987)].

Other yeast promoters, which are inducible have the additional advantage of transcription controlled by growth conditions, include the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

Yeast expression vectors can be constructed for intracellular production or secretion of a prostate tumor antigen from the DNA encoding the prostate tumor antigen of interest. For example, a selected signal peptide and the appropriate constitutive or inducible promoter may be inserted into suitable restriction sites in the selected plasmid for direct intracellular expression of the prostate tumor antigen polypeptide. For secretion of the prostate tumor antigen, DNA encoding the prostate tumor antigen polypeptide can be cloned into the selected plasmid, together with DNA encoding the promoter, the yeast alpha-factor secretory signal/leader sequence, and linker sequences (as needed), for expression of the prostate tumor antigen polypeptide.

Yeast cells, can then be transformed with the expression plasmids described above, and cultured in an appropriate fermentation media. The protein produced by such transformed yeast can then be concentrated by precipitation with 10% trichloroacetic acid and analyzed following separation by SDS-PAGE and staining of the gels with Coomassie Blue stain.

The recombinant prostate tumor antigen can subsequently be isolated and purified from the fermentation medium by techniques known to those of skill in the art.

c. Expression in Mammalian Systems. The prostate tumor antigen proteins may be expressed in mammalian cells. Mammalian expression systems are known in the art, and include retroviral vector mediated expression systems. Mammalian host cells may be transformed with any of a number of different viral-based expression systems, such as adenovirus, where the coding region can be ligated into an adenovirus transcription/translation complex consisting of the late promoter and tripartite leader sequence. Insertion in a nonessential E1 or E3 region of the viral genome results in a viable virus capable of expression of the polypeptide of interest in infected host cells.

A preferred expression vector system is a retroviral vector system such as is generally described in PCT/US97/01019 and PCT/US97/01048, both of which are hereby expressly incorporated by reference.

Suitable mammalian expression vectors contain a mammalian promoter which is any DNA sequence capable of binding mammalian RNA polymerase and initiating the downstream (3') transcription of a coding sequence for prostate tumor antigen protein into mRNA. A promoter will have a transcription initiating region, which is usually placed proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range.

Examples include promoters obtained from the genomes of viruses such as polyoma virus, fowlpox virus (UK 2,211, 504 published Jul. 5, 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding a prostate tumor antigen polypeptide by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer, the cytomegalovirus early promoter enhancer, the polyoma enhancer on the late side of the replication origin, and adenovirus enhancers. The enhancer is preferably located at a site 5' from the promoter.

In general, the transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenylation signals include those derived from SV40.

Long-term, high-yield production of recombinant proteins can be effected in a stable expression system. Expression vectors which contain viral origins of replication or endogenous expression elements and a selectable marker gene may be used for this purpose. Appropriate vectors containing selectable markers for use in mammalian cells are readily available commercially and are known to persons skilled in the art. Examples of such selectable markers include, but are not limited to herpes simplex virus thymidine kinase and adenine phosphoribosyltransferase for use in tk- or hprt-cells, respectively.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

d. Expression in Insect Cells. Prostate tumor antigen polypeptides may also be produced in insect cells. Expression vectors for the transformation of insect cells, and in particular, baculovirus-based expression vectors, are well known in the art. In one such system, the prostate tumor antigen-encoding DNA is fused upstream of an epitope tag contained within a baculovirus expression vector. *Autographa californica* nuclear polyhedrosis virus (AcNPV) is used as a vector to express foreign genes in *Spodoptera frugiperda* Sf9 cells or in Trichoplusia larvae. The prostate tumor antigen-encoding sequence is cloned into a nonessential region of the virus, such as the polyhedrin gene, and placed under control of the polyhedrin promoter. Successful insertion of a prostate tumor antigen-encoding sequence will render the polyhedrin gene inactive and produce recombinant virus lacking coat protein coat. The recombinant viruses are then used to infect *S. frugiperda* cells or Trichoplusia larvae in which the prostate tumor antigen is expressed [Smith et al., *J. Virol.* 46:584 (1994); Engelhard E K et al., *Proc. Nat. Acad. Sci.* 91:3224–3227 (1994)].

Suitable epitope tags for fusion to the prostate tumor antigen-encoding DNA include poly-his tags and immunoglobulin tags (like Fc regions of IgG). A variety of plasmids may be employed, including commercially available plasmids such as pVL1393 (Novagen). Briefly, the prostate tumor antigen-encoding DNA or the desired portion of the prostate tumor antigen-encoding DNA is amplified by PCR with primers complementary to the 5' and 3' regions. The 5' primer may incorporate flanking restriction sites. The PCR product is then digested with the selected restriction enzymes and subcloned into an expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL), or other methods known to those of skill in the art. Virus is produced by day 4–5 of culture in Sf9 cells at 28° C., and used for further amplifications. Procedures are performed as further described in O'Reilley et al., *BACULOVIRUS EXPRESSION VECTORS: A LABORATORY MANUAL*, Oxford University Press (1994).

Extracts may be prepared from recombinant virus-infected Sf9 cells as described in Rupert et al., *Nature* 362:175–179 (1993).

Alternatively, expressed epitope-tagged prostate tumor antigen polypeptides can be purified by affinity chromatography, or for example, purification of an IgG tagged (or Fc tagged) prostate tumor antigen polypeptide can be performed using chromatography techniques, including Protein A or protein G column chromatography.

D. Evaluation of Gene Expression

Gene expression may be evaluated in a sample directly, for example, by standard techniques known to those of skill in the art, e.g., Southern blotting for DNA detection, Northern blotting to determine the transcription of mRNA, dot blotting (DNA or RNA), or in situ hybridization, using an appropriately labeled probe, based on the sequences provided herein. Alternatively, antibodies may be used in assays for detection of nucleic acids, such as specific duplexes, including DNA duplexes, RNA duplexes, and DNA-RNA hybrid duplexes or DNA-protein duplexes. Such antibodies may be labeled and the assay carried out where the duplex is bound to a surface, so that upon the formation of duplex on the surface, the presence of antibody bound to the duplex can be detected.

Gene expression, alternatively, may be measured by immunohistochemical staining of cells or tissue sections and assay of cell culture or body fluids, to directly evaluate the expression of prostate tumor antigens. Antibodies useful for such immunological assays may be either monoclonal or polyclonal, and may be prepared against a native sequence prostate tumor antigen based on the DNA sequences provided herein.

1. Purification of Expressed Protein. Expressed prostate tumor antigen polypeptides may be purified or isolated after expression, using any of a variety of methods known to those skilled in the art. The appropriate technique will vary depending upon what other components are present in the sample. Contaminant components that are removed by isolation or purification are materials that would typically interfere with diagnostic or therapeutic uses for the polypeptide, and may include enzymes, hormones, and other solutes. The purification step(s) selected will depend, for example, on the nature of the production process used and the particular prostate tumor antigen polypeptide produced. A prostate tumor antigen polypeptide or protein may be recovered from culture medium or from host cell lysates. If membrane-bound, it can be released from the membrane using a suitable detergent solution (e.g. Triton-X 100) or by enzymatic cleavage. Alternatively, cells employed in expression of prostate tumor antigen polypeptides can be disrupted by various physical or chemical means, such as freeze-thaw cycling, sonication, mechanical disruption, or by use of cell lysing agents.

Exemplary purification methods include, but are not limited to, ion-exchange column chromatography; chromatography using silica gel or a cation-exchange resin such as DEAE; gel filtration using, for example, Sephadex G-75; protein A Sepharose columns to remove contaminants such as IgG; chromatography using metal chelating columns to bind epitope-tagged forms of the prostate tumor antigen polypeptide; ethanol precipitation; reverse phase HPLC; chromatofocusing; SDS-PAGE; and ammonium sulfate precipitation. Ordinarily, an isolated prostate tumor antigen polypeptide will be prepared by at least one purification step. For example, the prostate tumor antigen protein may be purified using a standard anti-prostate tumor antigen antibody column. Ultrafiltration and dialysis techniques, in conjunction with protein concentration, are also useful (see, for example, Scopes, R., *PROTEIN PURIFICATION*, Springer-Verlag, New York, N.Y., 1982). The degree of purification necessary will vary depending on the use of the prostate tumor antigen. In some instances no purification will be necessary.

Once expressed and purified as needed, the prostate tumor antigen proteins and nucleic acids of the present invention are useful in a number of applications, as detailed below.

2. Labeling of Expressed Protein. The nucleic acids, proteins and antibodies of the invention may be labeled. By labeled herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position that does not interfere with the biological activity or characteristic of the compound which is being detected.

3. Prostate Tumor Antigen Fusion Proteins. The prostate tumor antigens of the present invention may also be modified in a way to form chimeric molecules comprising a prostate tumor antigen fused to another, heterologous polypeptide or amino acid sequence. The term "fusion protein" used herein refers to a chimeric polypeptide comprising a prostate tumor antigen polypeptide, or domain sequence thereof, fused to a "targeting polypeptide". The targeting polypeptide has enough residues to facilitate targeting to a particular cell type or receptor, yet is short enough such that it does not interfere with the biological function of the prostate tumor antigen polypeptide. The targeting polypeptide preferably is also fairly unique so that the fusion protein does not substantially cross-react with other cell types or receptors. Suitable targeting polypeptides generally have at least about 10 amino acid residues and usually between from about 10 to about 500 amino acid residues. Preferred targeting polypeptides have from about 20 to about 200 amino acid residues.

The fusion protein may also comprises a fusion of a prostate tumor antigen with a tag polypeptide which provides an epitope to which an anti-tag antibody can selectively bind. The epitope tag is generally placed at the amino-or carboxyl-terminus of the prostate tumor antigen. Such epitope-tagged forms of a prostate tumor antigen can be detected using an antibody against the tag polypeptide. Also, provision of the epitope tag enables the prostate tumor antigen to be readily purified by using an anti-tag antibody or another type of affinity matrix that binds to the epitope tag. Alternatively, the fusion protein may comprise a fusion of a prostate tumor antigen with an immunoglobulin or a particular region of an immunoglobulin. For a bivalent form of the chimeric molecule, such a fusion could be to the Fc region of an IgG molecule or, for example, GM-CSF. Preferred fusion proteins include, but are not limited to, molecules that facilitate immune targeting of the prostate tumor antigen.

The prostate tumor antigen fusion protein may be made for various other purposes using techniques well known in the art. For example, for the creation of antibodies, if the desired epitope is small, a partial or complete prostate tumor antigen protein may be fused to a carrier protein to form an immunogen. Alternatively, the prostate tumor antigen protein may be made as a fusion protein to increase the ability of the antigen to stimulate cellular and/or humoral (antibody-based) immune responses, or for other reasons.

E. Anti-Prostate Tumor Antigen Antibodies

The present invention further provides anti-prostate tumor antigen antibodies. The antibodies of the present invention include polyclonal, monoclonal, humanized, bispecific, and heteroconjugate antibodies.

1. Polyclonal Antibodies. The anti-prostate tumor antigen antibodies of the present invention may be polyclonal antibodies. Methods of preparing polyclonal antibodies are known to the skilled artisan. Such polyclonal antibodies can be produced in a mammal, for example, following one or more injections of an immunizing agent, and preferably, an adjuvant. Typically, the immunizing agent and/or adjuvant will be injected into the mammal by a series of subcutaneous or intraperitoneal injections. The immunizing agent may include a prostate tumor antigen or a fusion protein thereof. It may be useful to conjugate the antigen to a protein known to be immunogenic in the mammal being immunized. Examples of such immunogenic proteins include, but are not limited to, keyhole limpet hemocyanin (KLH), serum albumin, bovine thyroglobulin, and soybean trypsin inhibitor. Adjuvants include, for example, Freund's complete adjuvant and MPL-TDM adjuvant (monophosphoryl Lipid A, synthetic trehalose dicoryno-mycolate). The immunization protocol may be determined by one skilled in the art based on standard protocols or by routine experimentation.

2. Monoclonal Antibodies. Alternatively, the anti-prostate tumor antigen antibodies may be monoclonal antibodies. Monoclonal antibodies may be produced by hybridomas, wherein a mouse, hamster, or other appropriate host animal, is immunized with an immunizing agent to elicit lymphocytes that produce or are capable of producing antibodies that will specifically bind to the immunizing agent [Kohler and Milstein, *Nature* 256:495 (1975)]. Alternatively, the lymphocytes may be immunized in vitro.

The immunizing agent will typically include the prostate tumor antigen or a fusion protein thereof. Generally, spleen cells or lymph node cells are used if non-human mammalian sources are desired, or peripheral blood lymphocytes ("PBLs") are used if cells of human origin. The lymphocytes are fused with an immortalized cell line using a suitable fusing agent, such as polyethylene glycol, to produce a hybridoma cell [Goding, *MONOCLONAL ANTIBODIES: PRINCIPLES AND PRACTICE,* Academic Press, pp. 59–103 (1986)]. In general, immortalized cell lines are transformed mammalian cells, for example, myeloma cells of rat, mouse, bovine or human origin. The hybridoma cells are cultured in a suitable culture medium that preferably contains one or more substances that inhibit the growth or survival of unfused, immortalized cells. For example, if the parental cells lack the enzyme hypoxanthine guanine phosphoribosyl transferase (HGPRT), the culture medium for the hybridomas typically will include hypoxanthine, aminopterin, and thymidine (HAT), substances which prevent the growth of HGPRT-deficient cells.

Preferred immortalized cell lines are those that fuse efficiently, support stable high level production of antibody, and are sensitive to a medium such as HAT medium. More preferred immortalized cell lines are murine or human myeloma lines, which can be obtained, for example, from the American Type Culture Collection (ATCC), Rockville, Md. Human myeloma and mouse-human heteromyeloma cell lines also have been described for the production of human monoclonal antibodies [Kozbor, *J. Immunol.* 133:3001 (1984); Brodeur et al., *MONOCLONAL ANTIBODY PRODUCTION TECHNIQUES AND APPLICATIONS,* Marcel Dekker, Inc., New York, pp. 51–63 (1987)].

The culture medium (supernatant) in which the hybridoma cells are cultured can be assayed for the presence of monoclonal antibodies directed against a prostate tumor antigen. Preferably, the binding specificity of monoclonal antibodies present in the hybridoma supernatant is determined by immunoprecipi-tation or by an in vitro binding assay, such as radio- immunoassay (RIA) or enzyme-linked immunoabsorbent assay (ELISA). Appropriate techniques and assays are known in the art. The binding affinity of the monoclonal antibody can, for example, be determined by the Scatchard analysis of Munson and Pollard, *Anal. Biochem.* 107:220 (1980).

After the desired antibody-producing hybridoma cells are identified, the cells may be cloned by limiting dilution procedures and grown by standard methods [Goding, 1986]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by selected clones may be isolated or purified from the culture medium or ascites fluid by immunoglobulin purification procedures routinely used by those of skill in the art such as, for example, protein A-Sepharose, hydroxyl-apatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be isolated from the prostate tumor antigen-specific hybridoma cells and sequenced, e.g., by using oligonucleotide probes that are capable of binding specifically to genes encoding the heavy and light chains of murine antibodies. Once isolated, the DNA may be inserted into an expression vector, which is then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for the human heavy and light chain constant domains in place of the homologous murine sequences [Morrison et al., *Proc. Nat. Acad. Sci.* 81:6851–6855 (1984); Neuberger et al., *Nature* 312:604–608 (1984); Takeda et al., *Nature* 314:452–454 (1985)], or by covalently joining to the immunoglobulin coding sequence all or part of the coding sequence for a non-immunoglobulin polypeptide. The non-immunoglobulin polypeptide can be substituted for the constant domains of an antibody of the invention, or can be substituted for the variable domains of one antigen-combining site of an antibody of the invention to create a chimeric bivalent antibody.

The antibodies may also be monovalent antibodies. Methods for preparing monovalent antibodies are well known in the art. For example, in vitro methods are suitable for preparing monovalent antibodies. Digestion of antibodies to produce fragments thereof, particularly, Fab fragments, can be accomplished using routine techniques known in the art.

3. Humanized Antibodies. The anti-prostate tumor antigen antibodies of the invention may further comprise humanized antibodies or human antibodies. The term "humanized antibody" refers to humanized forms of non-human (e.g., murine) antibodies that are chimeric antibodies, immunoglobulin chains or fragments thereof (such as Fv, Fab, Fab', F(ab')$_2$ or other antigen-binding partial sequences of antibodies) which contain some portion of the sequence derived from non-human antibody. Humanized antibodies include human immunoglobulins in which residues from a complementary determining region (CDR) of the human immunoglobulin are replaced by residues from a CDR of a non-human species such as mouse, rat or rabbit having the desired binding specificity, affinity and capacity. In general, the humanized antibody will comprise substantially all of at least one, and generally two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature* 321:522–525 (1986) and Presta, *Curr. Op. Struct. Biol.* 2:593–596 (1992)].

Methods for humanizing non-human antibodies are well known in the art. Generally, a humanized antibody has one or more amino acids introduced into it from a source which is non-human in order to more closely resemble a human antibody, while still retaining the original binding activity of the antibody. Methods for humanization of antibodies are further detailed in Jones et al., *Nature* 321:522–525 (1986); Riechmann et al., *Nature* 332:323–327 (1988); and Verhoeyen et al., *Science* 239:1534–1536 (1988).

Such "humanized" antibodies are chimeric antibodies in that substantially less than an intact human variable domain has been substituted by the corresponding sequence from a non-human species.

4. Heteroconjugate Antibodies. Heteroconjugate antibodies which comprise two covalently joined antibodies, are also within the scope of the present invention. Heteroconjugate antibodies may be prepared in vitro using known methods in synthetic protein chemistry, including those involving crosslinking agents. For example, immunotoxins may be prepared using a disulfide exchange reaction or by forming a thioether bond.

5. Bispecific Antibodies. Bispecific antibodies have binding specificities for at least two different antigens. Such antibodies are monoclonal, and preferably human or humanized. One of the binding specificities of a bispecific antibody of the present invention is for a prostate tumor antigen, and the other one is preferably for a cell-surface protein or receptor or receptor subunit.

Methods for making bispecific antibodies are known in the art, and in general, the recombinant production of bispecific antibodies is based on the co-expression of two immunoglobulin heavy-chain/light-chain pairs in hybridoma cells, where the two heavy chains have different specificities [Milstein and Cuello, *Nature* 305:537–539 (1983)]. Given that the random assortment of immunoglobulin heavy and light chains results in production of potentially ten different antibody molecules by the hybridomas, purification of the correct molecule usually requires some sort of affinity purification, e.g. affinity chromatography.

III. Utility

A. Polynucleotides

Polynucleotide sequences (or the complement thereof) which encode prostate tumor antigen polypeptides have various applications, including uses as hybridization probes, in chromosome and gene mapping, and in the generation of anti-sense RNA and DNA. In addition, prostate tumor antigen-encoding nucleic acids are useful as targets for pharmaceutical intervention, e.g. for the development of DNA vaccines, and for the preparation of prostate tumor antigen polypeptides by recombinant techniques, as described herein. The polynucleotides described herein, including sequence variants thereof, can be used in diagnostic assays, particularly for the detection of tumor cells. An important feature of the present invention is that the described sequences are currently recognized as specific to prostate tumor cells, but may also be characteristic of other tumor cells as well. Accordingly, diagnostic methods based on detecting the presence of such polynucleotides in body fluids or tissue samples are a feature of the present invention.

Examples of nucleic acid based diagnostic assays in accordance with the present invention include, but are not limited to, hybridization assays, e.g., in situ hybridization, and PCR-based assays. Polynucleotides, including extended length polynucleotides, sequence variants and fragments thereof, as described herein, may be used to generate hybridization probes or PCR primers for use in such assays. Such probes and primers will be capable of detecting polynucleotide sequences, including genomic sequences, that are similar, or complementary to, the tumor-specific polynucleotides described herein.

Hybridization probes can be used, for example, in performing in situ hybridization on tissue samples, such as fixed or frozen tissue sections prepared on microscopic slides or suspended cells. Briefly, a labeled DNA or RNA probe is allowed to bind its DNA or RNA target sample in the tissue section on a prepared microscopic, under controlled conditions. Generally, dsDNA probes consisting of the DNA of interest cloned into a plasmid or bacteriophage DNA vector are used for this purpose, although ssDNA or ssRNA probes may also be used. Probes are generally oligonucleotides between about 15 and 40 nucleotides in length. Alternatively, the probes can be polynucleotide probes generated by PCR random priming primer extension or in vitro transcription of RNA from plasmids (riboprobes). These latter probes are typically several hundred base pairs in length. The probes can be labeled by any of a number of methods, including fluorescent tags, enzymes or radioactive moieties, according to methods well known in the art. The particular detection method will correspond to the type of label utilized on the probe (e.g., autoradiography, X-ray detection, fluorescent or visual microscopic analysis, as appropriate). The reaction can be further amplified in situ using immunocytochemical techniques directed against the label of the detector molecule used, such antibodies directed to a fluorescein moiety present on a fluorescently labeled probe, or against avidin, or marker enzymes (peroxidase, alkaline phosphatase). Specific labeling and in situ detection methods can be found, for example, in Howard, G. C., Ed., *Methods in Nonradioactive Detection,* Appleton & Lange, Norwalk, Conn., (1993), herein incorporated by reference.

One preferred assay for detecting prostate tumor cells utilizes the subject polynucleotides, or fragments thereof, as primers in a PCR-based assay. According to the assay, nucleic acids present in a test tissue or cell sample are amplified by polymerase chain reaction (PCR) using two primers consisting of at least 15 nucleotides derived from one or more of a group consisting of SEQ ID NOs: 1–8 and 14, including primers derived from variants and/or extensions of such sequences, as described herein. Amplification products are detected in the sample by a method that is appropriate to the particular label used to label the amplification products, according to methods as described in U.S. Pat. No. 4,683,195. For use in PCR detection methods, such as PCR in situ hybridization, PCR primers are selected to be at least 15 nucleotides in length, and preferably between about 15 and 30 nucleotides in length, and are selected from the DNA molecule of interest, according to methods known in the art. While such primers can be selected from within the sequences identified as SEQ ID NO: 1 to SEQ ID NO: 8 and SEQ ID NOs: 14, herein, it may also be desirable to select sequences that encompass the longer nucleotide sequences. Preferably, the probes are selected such that the two hybridization sites are separated by between about 100–1,000 nucleotides (occasionally up to about 10,000 nucleotides).

PCR in situ hybridization of tissue sections and/or cell samples provides a highly sensitive detection method for rare cell types in fixed cell or tissue samples. The PCR in situ hybridization detection method is carried out in accordance with methods that are known in the art, e.g., Nuovo, G. J., *PCR IN SITU HYBRIDIZATION: PROTOCOLS AND APPLICATIONS,* Raven Press, N.Y., 1992; U.S. Pat. No. 5,538,871, both of which are incorporated herein by reference.

Briefly, a cell sample (tissue on microscopic slide, pelleted cell suspension) is fixed using a common fixative preparation, such as buffered formalin, formaldehyde or the like. Proteinase or detergent treatment is favored following fixation, to increase cell permeability to reagents. The PCR reaction is carried out in situ by polymerase chain reaction (PCR) using two primers. As discussed above, the primers are designed to selectively amplify one or more of the nucleotide sequences described herein, and particularly sequences described as SEQ ID NO: 1 to SEQ ID NO: 8 and SEQ ID NO: 14. The amplification reaction mixture contains, in addition to the target nucleotide sample and the primers, a thermostable DNA polymerase, such as a polymerase derived from *Thermus aquaticus* (Taq polymerase, U.S. Pat. 4,889,818), and a sufficient quantity of the four standard deoxyribonucleotides (dNTPs), one or more of which may be labeled to facilitate detection. The reaction mixture is subjected to several rounds of thermocycling to produce multiple copies (amplification products) of the target nucleotide sequence. Amplification products are then detected in the sample, for example by detecting radioactively labeled amplification products.

Hybridization probes and PCR primers may also be selected from the genomic sequences corresponding to the full-length proteins identified in accordance with the present invention, including promoter, enhancer elements and introns of the gene encoding the naturally occurring polypeptide.

Nucleotide sequences encoding a prostate tumor antigen polypeptide can also be used to construct hybridization probes for mapping the gene which encodes that prostate tumor antigen and for the genetic analysis of individuals. The nucleotide sequences provided herein may be mapped to a chromosome and specific regions of a chromosome using known techniques, such as in situ hybridization, linkage analysis against known chromosomal markers, and hybridization screening with libraries. Briefly, sequences can be mapped to chromosomes by preparing PCR primers (preferably 15–25 bp) from the prostate tumor antigen cDNA. Computer analysis of the 3' untranslated region is used to rapidly select primers that do not span more than one exon in the genomic DNA, which would complicate the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Individuals carrying variations of, or mutations in the gene encoding a prostate tumor antigen of the present invention may be detected at the DNA level by a variety of techniques. Nucleic acids used for diagnosis may be obtained from a patient's cells, including, for example, tissue biopsy and autopsy material. Genomic DNA may be used directly for detection or may be amplified enzymatically by using PCR [Saiki, et al. *Nature* 324:163–166 (1986)] prior to analysis. RNA or cDNA may also be used for the same purpose. As an example, PCR primers complementary to the nucleic acid of the present invention can be used to identify and analyze mutations in the gene of the present invention. Deletions and insertions can be detected by a change in size of the amplified product in comparison to the normal genotype.

Point mutations can be identified by hybridizing amplified DNA to radiolabeled RNA of the invention or alternatively, radiolabeled antisense DNA sequences of the invention. Sequence changes at specific locations may also be revealed by nuclease protection assays, such RNase and S1 protection or the chemical cleavage method [e.g. Cotton, et al., *Proc. Natl. Acad. Sci. USA* 85:4397–4401 (1985)], or by differences in melting temperatures. "Molecular beacons" [Kostrikis L. G. et al., *Science* 279:1228–1229 (1998)], hairpin-shaped, single-stranded synthetic oligonucleotides containing probe sequences which are complementary to the nucleic acid of the present invention, may also be used to detect point mutations or other sequence changes as well as monitor expression levels of prostate tumor antigens.

Polynucleotides which encode a prostate tumor antigen, or complements of such polynucleotides, may also be used for therapeutic purposes. Expression of a prostate tumor antigen may be modulated through antisense technology, which controls gene expression through complementary polynucleotides, i.e. antisense DNA or RNA, to the control, 5' or regulatory regions of the gene encoding the prostate tumor antigen. For example, the 5' coding portion of the polynucleotide sequence which codes for the protein of the present invention is used to design an antisense oligonucleotide of from about 10 to 40 base pairs in length. Oligonucleotides derived from the transcription start site, e.g. between positions −10 and +10 from the start site, are preferred. An antisense DNA oligonucleotide is designed to be complementary to a region of the gene involved in transcription [Lee et al., *Nucl. Acids Res.* 6:3073 (1979); Cooney et al., *Science* 241:456 (1988); and Dervan et al. *Science* 251:1360 (1991)], thereby interfering with or preventing transcription and the subsequent production of the prostate tumor antigen. An antisense RNA oligonucleotide hybridizes to the mRNA in vivo and blocks translation of the mRNA molecule into the prostate tumor antigen protein [Okano, *J. Neurochem.* 56:560 (1991)]. The antisense constructs can be delivered to cells by procedures known in the art such that the antisense RNA or DNA may be expressed in vivo.

The therapeutic polynucleotides of the present invention may be employed in combination with a suitable pharmaceutical carrier. Such compositions comprise a therapeutically effective amount of the compound, and a pharmaceutically acceptable carrier or excipient. Such a carrier includes but is not limited to saline, buffered saline, dextrose, water, glycerol, ethanol, and combinations thereof. The formulation is selected according to the mode of administration.

Prostate tumor antigen polypeptides, as well as agonist or antagonist polypeptides which modulate the biological activity thereof, may be employed in accordance with the present invention by expression of such polypeptides in vivo (i.e. "gene therapy"). Cells from a patient may be engineered to incorporate a polynucleotide (DNA or RNA) encoding such a polypeptide ex vivo, with the engineered cells then administered to a patient. Such treatment methods are known in the art. For example, cells may be engineered by use of a retroviral particle containing RNA encoding a polypeptide of the present invention.

Alternatively, cells may be engineered in vivo for expression of a polypeptide in vivo by procedures known in the art. By way of example, a producer cell capable of producing a retroviral particle containing RNA encoding a polypeptide of the present invention may be administered to a patient for engineering of cells and expression, with both steps taking place in vivo. The expression vehicle for engineering cells may be other than a retrovirus, for example, an adenovirus which may be used to engineer cells in vitro or in vivo for subsequent in vivo administration in a suitable delivery vehicle [see. For example, Griscelli, et al., *Proc. Nat. Acad. Sci.* 95:6367–6372 (1998)].

Nucleic acids which encode a prostate tumor antigen polypeptide or any of its modified forms can also be used to generate either transgenic animals or "knock out" animals which, in turn, are useful in the development and screening of therapeutically useful reagents. A trans-genic animal, such as a mouse or rat is an animal having cells that contain a transgene, which transgene was introduced into the animal or an ancestor of the animal at a prenatal, e.g., an embryonic stage. A transgene is DNA which is integrated into the genome of a cell from which the transgenic animal develops. A cDNA encoding prostate tumor antigen can be incorporated into genomic DNA in accordance with established techniques, with the genomic DNA used to generate transgenic animals that contain cells which express the prostate tumor antigen. Methods for generating transgenic animals, particularly animals such as mice and rats, have become conventional in the art and are described, for example, in U.S. Pat. Nos. 4,736,866 and 4,870,009. Such transgenic animals can be used to examine the effect of modified expression of DNA encoding a particular prostate tumor antigen. Such animals can be used as tester animals for reagents thought to confer protection from, for example, pathological conditions associated with the expression or overexpression of a particular prostate tumor antigen. Accordingly, an animal is treated with the reagent and a reduced incidence of a pathological condition associated with a particular prostate tumor antigen, compared to untreated animals bearing the transgene, would indicate a potential therapeutic intervention for the pathological condition.

Alternatively, non-human homologues of a prostate tumor antigen can be used to construct a "knock out" animal which has a defective or altered gene encoding a selected prostate tumor antigen. For example, cDNA encoding the prostate tumor antigen can be used to clone genomic DNA encoding a prostate tumor antigen in accordance with established techniques. A portion of the genomic DNA encoding the prostate tumor antigen can be deleted or replaced with another gene, such as a gene encoding a selectable marker which can be used to monitor integration. Typically, several kilobases of unaltered flanking DNA (both at the 5' and 3' ends) are included in the vector [see for example, Thomas and Capecchi, *Cell* 51:503 (1987)]. The vector is introduced into an embryonic stem cell line and cells in which the introduced DNA has homologously recombined with the endogenous DNA are selected [see e.g., Li et al., *Cell* 69:915 (1992)]. The selected cells are then injected into a blastocyst of an animal (e.g., a mouse or rat) to form aggregation chimeras [see e.g., Bradley, in *TERATOCARCINOMAS AND EMBRYONIC STEM CELLS: A PRACTICAL APPROACH,* E. J. Robertson, ed., IRL, Oxford, 113–152 (1987)]. A chimeric embryo can then be implanted into a suitable female foster animal and the embryo brought to term to create a "knock out" animal. Progeny harboring the homologously recombined DNA in their germ cells can be identified by standard techniques. Knockout animals can be characterized for instance, for the absence of a pathological condition normally associated with a selected prostate tumor antigen.

B. Polypeptides

Similarly, knowledge of the full-length, and in some cases the partial nucleotide sequences provided herein, provides the basis for identifying the various polypeptides encoded by the nucleotides described herein. Such polypeptide antigens, or immunogenic fragments thereof, can be used, for example, to elicit an immune response (humoral or cellular) in a host organism for the purpose of eradicating tumor cells present in the organism, or to stimulate production of polyclonal and/or monoclonal antibodies for therapy or for use in diagnostic kits in accordance with the present invention. The polypeptides of the present invention have numerous uses including, but not limited to, utility in producing vaccines against tumor-specific antigens. Such vaccines may be formulated to produce a humoral (antibody) or cellular immune response in the target organism. Generally, vaccine compositions may be produced using full-length polypeptides or antigenic peptides, where the latter are generally conjugated to an immunogenic carrier and cellular immune stimulatory compositions may be produced according to methods such as described in co-owned, co-pending U.S. Application No. 08/579,823, incorporated herein by reference.

Polypeptides in accordance with the present invention may also find utility in detection methods, such as in radioimmunoassay- and ELISA-based diagnostic assays. Such polypeptides may also be used to produce antibodies to be used as reagents in such assays. The set up and optimization of such assays is within the skill of those practiced in the art of assay development.

The present invention also includes a method for identifying a receptor for a prostate tumor antigen. The gene encoding a prostate tumor antigen-receptor can be identified by numerous methods known to those of skill in the art, for example, ligand panning and FACS sorting [Coligan, et al., *Current Protocols in Immunol.* 1(2), Chapter 5 (1991)]. Preferably, expression cloning is employed wherein polyadenylated RNA is prepared from a cell responsive to prostate tumor antigen, and a cDNA library created from this RNA is divided into pools and used to transfect COS cells or other cells that are not responsive to prostate tumor antigen. Transfected cells which are grown on glass slides are exposed to labeled prostate tumor antigen. The prostate tumor antigen can be labeled by a variety of means including iodination or inclusion of a recognition site for a site-specific protein kinase. Following fixation and incubation, the slides are subjected to autoradiographic analysis. Positive pools are identified and sub-pools are prepared and retransfected using an iterative sub-pooling and rescreening process, eventually yielding a single clone that encodes the putative receptor.

As an alternative approach for receptor identification, labeled prostate tumor antigen can be photoaffinity linked with cell membrane or extract preparations that express a receptor molecule. Cross- linked material is resolved by PAGE and exposed to X-ray film. A labeled complex containing the prostate tumor antigen-receptor can be excised, resolved into peptide fragments, and subjected to protein microsequencing. The amino acid sequence obtained from microsequencing can be used to design a set of degenerate oligonucleotide probes to screen a cDNA library to identify the gene encoding a putative receptor.

The present invention also includes methods for identifying molecules, such as synthetic drugs, antibodies, peptides, or other molecules, which have a modulating effect on the activity of the prostate tumor antigen e.g. agonists or antagonists of the prostate tumor antigen-receptor.

When a prostate tumor antigen binds to another protein, for example, when the prostate tumor antigen functions as a receptor, the prostate tumor antigen can be used in assays to identify other proteins or molecules which may participate in the binding interaction. By such methods, inhibitors of the receptor/ligand binding interaction can be identified. Proteins involved in such binding interactions can also be used to screen for peptide or small molecule inhibitors or agonists of the binding interaction.

Screening assays can be designed to find compounds that modulate the biological activity of a native prostate tumor antigen or a receptor for such a prostate tumor antigen. Preferred screening assays will be amenable to high-throughput screening of chemical libraries, making them particularly suitable for identifying small molecule drug candidates. Small molecules contemplated include synthetic organic or inorganic compounds. The assays can be performed in a variety of formats, including protein—protein binding assays, biochemical screening assays, immunoassays and cell based assays, all of which are well characterized in the art.

C. Antibodies

A prostate tumor antigen polypeptide may also be used to generate antibodies, however, the prostate tumor antigen polypeptide must share at least one epitope or determinant with the full length protein sequence shown in any one of FIGS. 9A–C or 11. By "epitope" or "determinant" herein is meant a portion of a protein which will generate and/or bind an antibody. Thus, in most instances, antibodies made to a smaller prostate tumor antigen polypeptide will be able to bind to the full length protein. It is preferred that the epitope be unique; that is, antibodies generated to the unique epitope show little or no cross-reactivity with other antigens. In other words, the antibodies of the invention specifically bind to prostate tumor antigens. By "specifically bind" herein is meant that the antibodies bind to the protein with a binding constant in the range of at least $10^6$–$10^8$ M, with a preferred range being $10^7$–$10^9$ M.

The anti-prostate tumor antigen antibodies of the present invention have various utilities, e.g., they may be used in diagnostic assays for the presence of prostate tumor antigen, such as detecting expression in specific cells, tissues, and/or serum. Various diagnostic assays known in the art may be used, such as competitive binding assays, direct or indirect sandwich assays and immunoprecipitation assays conducted in either heterogeneous or homogeneous phases [Zola, *MONOCLONAL ANTIBODIES: A MANUAL OF TECHNIQUES*, CRC Press, Inc., 147–158 (1987)]. The antibodies used in such diagnostic assays can be labeled with a detectable label. The detectable label should be capable of producing, either directly or indirectly, a detectable signal. For example, the detectable label may be a radioisotope, such as $^3H$, $^{14}C$, $^{32}P$, $^{35}S$, or $^{125}I$, a fluorescent or chemiluminescent compound, such as fluorescein isothiocyanate (FITC), rhodamine, or luciferin, or an enzyme, such as alkaline phosphatase, beta-galactosidase or horseradish peroxidase. Any method known in the art for conjugating the antibody to the detectable label may be employed, including those methods described by Hunter et al., *Nature* 144:945 (1962); David et al., *Biochemistry* 13:1014 (1974); Pain et al., *J. Immunol. Meth.* 40:219 (1981); and Nygren, *J. Histochem. and Cytochem.* 30:407 (1982).

Anti-prostate tumor antigen antibodies are useful for the affinity purification of prostate tumor antigens from recombinant cell culture or natural sources. In this process, the antibodies against a prostate tumor antigen are immobilized on a suitable support, such a Sephadex resin or filter paper, using methods well known in the art. The immobilized antibody is then contacted with a sample containing the prostate tumor antigen to be purified, and thereafter the support is washed with a suitable solvent that will remove substantially all the material in the sample except the prostate tumor antigen, which is bound to the immobilized antibody. Finally, the support is washed with another suitable solvent that will release the prostate tumor antigen from the antibody.

The prostate tumor antibodies of the present invention are capable of reducing or eliminating the biological function of the prostate tumor antigen with which they specifically react. That is, the addition of either polyclonal or preferably monoclonal anti-prostate tumor antigen antibodies to cells comprising prostate tumor receptors may reduce or eliminate the pathology associated with the presence of a prostate tumor. Generally, at least a 50% decrease in activity is preferred, with at least about 75% being more preferred at least about 85–90% being particularly preferred and about a 95–100% decrease being especially preferred.

Anti-prostate tumor antibody compositions are tested in appropriate in vitro and in vivo animal models of disease, to confirm specificity, efficacy, tissue metabolism, and to estimate dosages, according to methods known in the art.

Anti-prostate tumor antibody compositions may be administered by any of a number of routes and methods designed to provide a consistent and predictable concentration of antibody at the target tissue. The antibody compositions may be administered alone, or in combination with other agents, such as stabilizing compounds, and/or in combination with other pharma-ceutical agents such as drugs or hormones. Therapeutic value may be achieved by administering one or more antibodies specific for a prostate tumor antigen. Such antibodies may be useful in preventing the interaction of a tumor antigen with its receptor.

A human or humanized monoclonal antibody is preferred in the therapeutic application of the present invention. The antibody is typically administered as a sterile solution by IV injection in an amount between about 1–15 mg/kg body weight of the subject, although other parenteral routes of administration may be suitable. Appropriate treatment regimens will vary depending upon the affinity of the particular antibody selected, the route of administration selected, the dose and patient condition. These parameters are easily determinable by the skilled practitioner using routine experimentation. In one exemplary method, the antibody treatment is used to inhibit tumor growth, by administering the antibody to the site of the tumor, and such administration is continued until a therapeutic improvement is seen.

A therapeutic composition for use in the treatment method can include the antibody in a sterile injectable solution, the antibody in an oral delivery vehicle, or the polypeptide in a nebulized form, all prepared according to well known methods. Such compositions comprise a therapeutically effective amount of the antibody, and a pharmaceutically acceptable carrier or excipient. Such a carrier includes but is not limited to saline, buffered saline, dextrose, water, glycerol, ethanol, and combinations thereof.

The following examples are offered for illustrative purposes only, and are not intended to limit the scope of the present invention in any way.

All patent and literature references cited in the present specification are hereby incorporated by reference in their entirety.

IV. Materials and Methods

A. Differential Display Detection Kit and Primers

A commercial differential display detection kit, "HIEROGLYPH mRNA Profile System" (GENOMYX Corp., Foster City, Calif.) was used to identify polynucleotides that are specific to prostate tumor cells. This system is designed to produce cDNA fragments of up to 1.2–1.5 kb in length with excellent reproducibility between duplicate samples. The HIEROGLYPH anchored primers incorporate a 17 nt T7 NA polymerase promoter-derived site (ACGACTCACTATAGGGC; SEQ ID NO: 12) to allow directional sequencing from the 3' end of the original mRNA transcript without requiring fragment/vector subcloning. The core annealing sequences of the arbitrary 5' primers used in the HIEROGLYPH system are 10 bases in length. Twenty different arbitrary upstream primers are used. Arbitrary Primers (ARPs) incorporate a 16-nt segment of the M13 universal reverse (148) 24 mer primer sequence, ACAATTTCACACAGCA, (SEQ ID NO: 13) which allows directional sequencing from the 5'-end of the original transcript. Each ARP is therefore 26 nt in length.

B. Enrichment of Subtracted Prostate cDNA

"Highly enriched" subtracted prostate cDNA was prepared by methods detailed in the cDNA Subtraction Kit from CLONTECH Laboratories (Palo Alto, Calif.). Briefly, tester cDNA was prepared from normal human prostate poly A+ RNA; the cDNA population that contains the tissue-specific sequences of interest. Driver cDNA was prepared from a mixture of poly A+ RNA prepared from 10 different tissues including spleen, thymus, brain, heart, kidney, liver, lung, ovary, placenta, and skeletal muscle.

Subtractive hybridization and primary PCR were performed using these two populations.

C. Cloning of Prostate Tumor Specific Nucleic Acids

All cloning procedures were carried out with commercially available kits according to protocols provided by the manufacturer. The subtracted prostate DNA was generated with the "Clontech PCR-select cDNA subtraction kit" (Clontech, Palo Alto, Calif.). Subcloning procedures were carried out with the "TA cloning kit" (Invitrogen, Carlsbad, Calif.).

EXAMPLE 1

Molecular Cloning of Genes from Prostate Tumor Cells

The mRNA expression patterns of normal prostate, the prostatic carcinoma cell line LNCaP (ATCC CRL 1740; American Type Culture Collection; Rockville, Md.) and of HeLa cells were compared by differential display (DD) using the HIEROGLYPH mRNA Profile System described above. All procedures were carried out essentially as described in the manufacturer's instructions provided as a package insert and incorporated herein by reference. Briefly, DNA-free total RNA was isolated from cell lines using the SNAP Total RNA kit (Invitrogen, San Diego, Calif.). RNA from prostatic tissue was commercially obtained from Clontech, Inc. (Palo Alto, CA) and was treated from Rnase free Dnase to remove genomic DNA contaminants. Qualitatively, the RNA had a minimum OD260/OD280 ratio of greater than 1.8. The RNA was determined to be intact by electrophoretic analysis.

First strand cDNA copies of the RNA transcripts were generated using commercially available transcriptase ("SUPERSCRIPT", Life Technologies, Rockville, Md.) and 3' "anchored" primers provided in the HIEROGLYPH kit. The reaction was carried out at 42% C. for one hour. The reverse transcribed RNA was then subjected to amplification by polymerase chain reaction (PCR) using duplicate reactions having pairwise combinations of ten anchored 3' and four arbitrary 5' primers. The anchored primers were identical to those used in the reverse transcriptase reaction. Also present in the reaction mixtures were AMPLITAQ DNA polymerase and [$\alpha$-$^{33}$P]dATP. Four PCR cycles were run at 46%, and 25 cycles were run at 60%. Reaction products were separated by electrophoresis on a 4.5% and/or a 6% HR-1000 gel followed by autoradiography of the resulting gels.

Twenty primer combinations were evaluated in duplicate experiments from each of the three mRNA sources, for a total of 120 PCR reactions. The DD-PCR fragments generated from the screening regimen were analyzed by gel electrophoresis on 33 (61 cm gels using the genomyxLR and HR-1000 gels). Autoradiographs of the gels were analyzed for bands that are specifically expressed only in the prostatic carcinoma cell line sample LnCaP but not in the HeLa carcinoma or in normal prostate. A total of 54 DD products were identified that met these criteria; the bands excised from the gels and reamplified by PCR. The PCR products were purified via agarose gel electrophoresis, and 5' ends were subjected to DNA sequencing by cycle sequencing with di-deoxy terminators. The sequence was obtained for all 54 fragments. The 54 fragments revealed 35 different mRNA transcripts, which were compared to daily updated database releases of GenBank, GenBank EST division and EMBL. A total of eight mRNAs/CDNAs were found to be novel, as evidenced by lack of significant database match with BLASTN or TBLASTX algorithms (Example 2, SEQ ID NO: 1–4, 6–8). SEQ ID NO: 5 was identified as a novel member of the thioredoxin reductase gene family by this method.

EXAMPLE 2

Screening of Selected Nucleotide Sequences

A. Sequence Identity Screening of SEQ ID 1–8

Nucleotide sequences were screened with the BLASTN and TBLASTX algorithm against the NCBI Entrez NR (May 6, 1997; 309920 sequences) and NCBI Entrez EST (May 6, 1997; 10155474 sequences) database releases. SEQ ID NOs: 1–4 and 6–8 were found to have no significant sequence similarity with any known sequences. SEQ ID NO: 5 was found to have substantial homology (approximately 78%) by BLASTN to an uncharacterized mouse EST. Amino acid sequences deduced from SEQ ID NO: 5, incorporated herein as SEQ ID NOs: 9–11, were also determined to have homology by TBLASTX with portions of mouse and human thioredoxin reductase, suggesting that the detected nucleotide sequence encodes a novel member of the thioredoxin reductase gene family.

B. Sequence Identity Screening of SP 1–4 Sequences

The SP 1–4 nucleotide sequence (SEQ ID NO: 14) was screened with the BLASTN and TBLASTX algorithms against the NCBI Entrez NR and NCBI Entrez EST database releases (Jul. 1, 1998). SEQ ID NO: 14 and partial sequences thereof were found to have less than about 45% sequence identity to any known nucleic acid sequence. The deduced SP 1–4 amino acid sequence, SEQ ID NO: 15, was found to have less than about 30% sequence identity to any known polypeptides over the entire length of the sequence using the BLASTP algorithm in a search comparing amino acids 1 to 1095 of SEQ ID NO: 15 to the "non-redundant Genbank CDS translations+PDB+SwissProt+Spupdate+PIR" database on Jul. 1, 1998, suggesting that the SP 1–4 nucleotide sequence encodes a novel protein.

EXAMPLE 3

Molecular Cloning of Human SP 1–4 cDNA

A. Isolation of Original Partial cDNA Insert

Human subtracted prostate cDNA, highly enriched for prostate specific partial cDNA sequences, was amplified using the primer pair as follows:

NP1 5'-TCGAGCGGCCGCCCGGGCAGGT-3' (SEQ ID NO: 16)

NP2 5'-AGGGCGTGGTGCGGAGGGCGGT-3' (SEQ ID NO: 17)

on a Perkin-Elmer GeneAmp 9600 Cycler for 11 cycles with the following thermal cycling profile: 94° C. for 10 sec; 68° C. for 30 sec; 72° C. for 5 min. This was followed by one additional round at 72° C. for 5 min. The products were ligated into the pCR2.1 TA cloning vector (Invitrogen) and transformed into E. coli. Individual ampicillin resistant bacterial transformants were screened by PCR for the presence of an insert using the primer pair as follows:

M13 Reverse 5'-CAGGAAACAGCTATGA-3' (SEQ ID NO: 18)

M13 Forward 5'-GTAAAACGACGGCCAGTG-3' (SEQ ID NO: 19)

and the following thermal cycling profile: 94° C. for 15 sec; 55° C. for 30 sec; 72° C. for 1 min. This was followed by one additional round at 72° C. for 6 min. The original SP 1–4 insert in the pCR2.1 plasmid was sequenced using the M13 reverse primer (SEQ ID NO: 18), and the M13–20 primer (SEQ ID NO: 19), on an ABI 373 DNA Sequencer. DNA sequences were analyzed using Sequencher 3.0 (Gene Codes Corporation, Ann Arbor, Mich.).

B. Isolation of Full Length SP 1–4 cDNA

Marathon cDNA from normal human prostate poly $A^+$ RNA was prepared for carrying out both 5' and 3' Rapid Amplification of cDNA Ends [RACE, Frohman et al., *Proc. Nat. Acad. Sci.* 85:8998–9002, (1988), Clontech Laboratories]. 5' RACE was carried out with the following primer pair:

AP1 5'-CCATCCTAATACGACTCACTATAGGGC-3' (SEQ ID NO: 20)

A79331 5- GCCGAGTAATAGGAGACACGTCGTGG-3' (SEQ ID NO: 21)

3' RACE was carried out with with the following primer pair:

AP1 5'-CCATCCTAATACGACTCACTATAGGGC-3' (SEQ ID NO: 20); and

A79326 5-TGGAAACTGGTTGCGAACTTCCG-3' (SEQ ID NO: 22)

The thermal cycling profile for all RACE reactions was 94° C. for 15 sec; 68° C. for 4 min for 30 cycles using Advantage cDNA Polymerase Mix (Clontech Laboratories). 5' and 3' RACE products of approximately 4 kb and 1.6 kb respectively were isolated by agarose gel electrophoresis, ligated into the pCR2.1 TA vector (Invitrogen), and transformed into competent E. coli cells. Individual ampicillin resistant bacterial colonies were screened by PCR for the presence of an insert with the following primer pair:

AP2 5'-ACTCACTATAGGGCTCGAGCGGC-3' (SEQ ID NO: 23)

A79331 5'-GCCGAGTAATAGGAGACACGTCGTGG-3' (SEQ ID NO: 21)

for the 5' RACE products and the following primer pair:

AP2 5'-ACTCACTATAGGGCTCGAGCGGC-3' (SEQ ID NO: 23)

A79328 5'-CAAAGTCATTTGGCAGCAGACCAGG-3' (SEQ ID NO: 24)

for the 3' RACE products using a thermal cycling profile of 94° C. for 15 sec; 55° C. for 30 sec; 72° C. for 1 min for 35 cycles, followed by one additional round at 72° C. for 6 min. PCR products were resolved by agarose gel electrophoresis, and individual bacterial transformants were grown in liquid culture (Luria-Broth supplemented with ampicillin 100 µg/ml) prior to preparation of plasmid DNA. The complete DNA sequence of individual RACE products was determined by automated fluorescent sequencing using an ABI 373 DNA sequencer in conjunction with custom DNA primers and the Primer Island Transposition Kit (PE Applied Biosystems).

The entire 5668 base pair nucleotide sequence designated SP 1–4 cDNA, is shown in FIG. 10 (SEQ ID NO: 14). The sequence contains a single open reading frame with an apparent translational initiation site at nucleotide positions 43–45 [Kozak et al., *Nucl. Acids Res.* 12:3873–3893 (1984)] with a stop codon at nucleotide positions 3328–3330 (FIG. 10).

The full-length SP 1–4 protein, (SEQ ID NO: 15), shown in FIG. 11 is 1095 amino acids long. Important regions of the amino acid sequence of the SP 1–4 protein include the transmembrane regions corresponding to amino acids 732–748, 846–876, 681–703, 789–805, 944–971, 820–837, and 999–1015, respectively, and potential N-glycosylation sites, beginning at amino acids 6, 75, 247, 308, 812, 925, 1041, and 1063, respectively. Clones pCR2.1/SP 1–4 (5' RACE, SEQ ID NO: 27) and pCR2.1/SP 1–4 (3' RACE, SEQ ID NO: 28) have been deposited with ATCC and are assigned ATCC deposit numbers 98827, 98828 and 98829, respectively.

EXAMPLE 4

Expression of Human SP 1–4

A. RT-PCR

First strand cDNA synthesis was prepared using human poly A+ RNA's and the SMART PCR cDNA Synthesis Kit (Clontech Laboratories). The primer pair A80552 5'-GATTTTCACCAATGACCGCCG-3' (SEQ ID NO: 25); and

A80553 5'-CCCCAGCAGCATTGATGTCG-3' (SEQ ID NO: 26)

was used to assess expression with a thermal cycling profile of 94° C. for 15 sec; 65° C. for 15 sec; 72° C. for 30 sec (30 cycles), followed by one additional round at 72° C. for 6 min. Amplification products were resolved by agarose gel electrophoresis and visualized by ethidium bromide staining and ultraviolet light.

As shown in Table 1 below, numerous samples were amplified and SP 1–4-specific mRNA expression clearly detected by RT-PCR in testis and prostate tissue, as well as in a colorectal adenocarcinoma cell line, (SW480), a melanoma tissue sample (G361) and in LNCaP which is a prostatic carcinoma cell line.

TABLE 1

| Sample | PCR Product |
|---|---|
| Spleen | neg |
| Mammary Gland | trace |
| Placenta | neg |
| Kidney | neg |
| Liver | neg |
| Lung | neg |
| Testis | + |
| SW480 (colorectal adenocarcinoma) | + |
| G361 (melanoma) | + |
| LNCaP | + |
| Prostate | ++ |
| PC3 | neg |
| DU145 | neg |
| Skeletal Muscle | neg |
| Bone Marrow | neg |
| Brain | neg |
| Heart | neg |
| A549 (lung carcinoma) | neg |
| Pancreas | neg |
| Intestine | neg |
| Thymus | trace |

B. Nucleic Acid Hybridization

The original insert isolated from the subtracted library was used as a hybridization probe for Northern blot and RNA dot blot analysis. The fragment was random primer labeled with $^{32}$P-dCTP, purified on a G-50 micro-spin column, and hybridized to filters using ExpressHyb Hybridization Solution (Clontech Laboratories) at 68° C. for 2–4 hours The filters were washed sequentially in 2×SSC [1×SSC=150 mM NaCl, 15 mM sodium citrate], 0.1% SDS at room temperature for 30 min, 0.5×SSC, 0.1% SDS at room temperature for 30 min, and 0.5×, 0.1% SDS at 65° C. for 30 min. Autoradiography was performed for one hour to one day at −70° C. using Kodak XAR film and a single intensifying screen.

The results of human RNA dot blot and Northern blot analysis of numerous tissues, both adult and fetal in origin as shown in Tables 2 and 3 below, respectively, indicate that SP 1–4- specific mRNA is preferentailly expressed in prostate tissue.

TABLE 2

| Sample | SP 1-4 Signal | Sample | SP 1-4 Signal |
|---|---|---|---|
| whole brain | neg | salivary gland | neg |
| amygdala | neg | mammary gland | neg |
| caudate nucleus | neg | kidney | trace |
| cerebellum | neg | liver | neg |
| cerebral cortex | neg | small intestine | neg |
| frontal lobe | neg | spleen | neg |
| hippocampus | neg | thymus | neg |
| medulla oblongata | neg | peripheral leukocyte | neg |
| occipital lobe | neg | lymph node | neg |
| putamen | neg | bone marrow | neg |
| substantia nigra | neg | appendix | neg |
| temporal lobe | neg | lung | neg |
| thalamus | neg | trachea | neg |
| subthalamic nucleus | neg | placenta | neg |
| spinal cord | neg | fetal brain | neg |
| heart | neg | fetal heart | neg |
| aorta | neg | fetal kidney | neg |
| skeletal muscle | neg | fetal liver | neg |
| colon | neg | fetal spleen | neg |
| bladder | neg | fetal thymus | neg |
| uterus | neg | fetal lung | neg |
| prostate | ++++ | pancreas | neg |
| stomach | neg | pituitary gland | neg |
| testis | trace | adrenal gland | neg |
| ovary | neg | thyroid gland | neg |

TABLE 3

| Sample | SP 1-4 Transcripts |
|---|---|
| HL-60 | neg |
| HeLA | neg |
| K562 | neg |
| Molt-4 | neg |
| Burkitts Lymphoma | neg |
| colorectal adenocarcinoma SW480 | neg |
| lung carcinoma A549 | neg |
| Melanoma G361 | + |
| skeletal muscle | neg |
| uterus | neg |
| colon | neg |
| small intestine | neg |
| bladder | neg |
| heart | neg |
| stomach | neg |
| prostate | +++++ |

While the invention has been described with reference to specific methods and embodiments, it will be appreciated that various modifications and changes may be made without departing from the invention.

It is claimed:

1. An isolated polynucleotide selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and the complement of any of said sequences.

2. The isolated polynucleotide of claim 1, wherein said polynucleotide is an RNA molecule.

3. An isolated polynucleotide having at least 95% sequence identity to nucleotides 43–3327 of the sequence of SEQ ID NO: 14, wherein % identity is calculated using the LALIGN program found in the FASTA Version 2.0 suit of programs using default parameters with the BLOSUM50 matrix, a ktup of 2 and a gap penalty of −12/−2, and wherein said isolated polynucleotide hybridizes to nucleotides 43–3327 of SEQ ID NO: 14 under high stringency conditions as follows: hybridization at 65 °C. in 5×SSPE and washing conditions of 65 °C. in 0.1×SSPE.

4. An isolated polynucleotide consisting of nucleotides 43–3327 of the nucleotide sequence of SEQ ID NO: 14.

5. A vector comprising the polynucleotide of any one of claims 1, 2, or 4 operably linked to control sequences recognized by a host cell transformed with said vector.

6. A host cell comprising the vector of claim 5.

7. A method of detecting tumor cells in a tissue sample, comprising (a) amplifying nucleic acids generated from said sample by polymerase chain reaction (PCR) using two primers, where said two primers are designed to selectively amplify a nucleic acid sequence which encodes a prostate-derived tumor antigen, said nucleic acid sequence presented as nucleotides 43 to 3327 of SEQ ID NO: 14; and (b) detecting the presence of amplification products that correspond to said sequence or amplified portions thereof.

* * * * *